(12) United States Patent
Smith et al.

(10) Patent No.: US 11,535,596 B2
(45) Date of Patent: Dec. 27, 2022

(54) ANALOGS OF DEXTROMETHORPHAN WITH BALANCED RECEPTOR ACTIVITIES

(71) Applicant: The Center for Neurologic Study, La Jolla, CA (US)

(72) Inventors: Richard Alan Smith, La Jolla, CA (US); Darryl C. Rideout, Milford, PA (US); Kathleen J. Myers, Oceanside, CA (US); Andrew Kawasaki, San Diego, CA (US)

(73) Assignee: Center for Neurologic Study, La Jolla, CA (US)

( * ) Notice: Subject to any disclaimer, the term of this patent is extended or adjusted under 35 U.S.C. 154(b) by 0 days.

(21) Appl. No.: 17/461,727

(22) Filed: Aug. 30, 2021

(65) Prior Publication Data

US 2022/0064122 A1    Mar. 3, 2022

Related U.S. Application Data

(60) Provisional application No. 63/072,053, filed on Aug. 28, 2020.

(51) Int. Cl.
*C07D 221/22*    (2006.01)
*A61P 29/00*    (2006.01)
*C07D 405/06*    (2006.01)

(52) U.S. Cl.
CPC ............ *C07D 221/22* (2013.01); *A61P 29/00* (2018.01); *C07D 405/06* (2013.01)

(58) Field of Classification Search
CPC ...... C07D 221/22; C07D 405/06; A61P 29/00
See application file for complete search history.

(56) References Cited

U.S. PATENT DOCUMENTS

| | | | |
|---|---|---|---|
| 8,710,072 B2 * | 4/2014 | Graham | A61K 31/4709 514/289 |
| 2009/0005270 A1 * | 1/2009 | Melker | C12Q 1/26 506/39 |

* cited by examiner

*Primary Examiner* — D Margaret M Seaman
(74) *Attorney, Agent, or Firm* — James P. Demers; Cittone, Demers & Arneri LLP

(57) ABSTRACT

Substituted analogs of dextromethorphan (DM) are disclosed, which are shown to have substantial binding affinity at both NMDA and sigma-1 receptors, and which are degraded by human liver enzymes more slowly than dextromethorphan. The analogs are useful as alternatives to dextromethorphan, and can provide the same benefits without requiring co-administration of a cytochrome P-450 enzyme inhibitor.

16 Claims, No Drawings

ANALOGS OF DEXTROMETHORPHAN WITH BALANCED RECEPTOR ACTIVITIES

RELATED APPLICATIONS

This application claims priority from U.S. provisional application No. 63/072,053 filed on Aug. 28, 2020, the entire contents of which are incorporated herein by reference.

FIELD OF THE INVENTION

This invention is in the fields of medicinal chemistry and pharmacology, more specifically the field of dextromethorphan analogues.

BACKGROUND

Dextromethorphan is a well-known drug commonly used as a therapeutic agent in cough syrups. Dextromethorphan, abbreviated as DM, is an enantiomer of levorphonal, an opiate drug, but poses little or no risk of addiction. The vast majority of its sales are as a cough suppressant in over-the-counter products that do not require a prescription from a physician.

Bolser, "Current and future centrally acting antitussives," Respir. Physiol. Neurobiol. 152(3):349-355 (2006). DM has also been investigated for its potential neuroprotective effects. Werling et al., "Dextromethorphan as a potential neuroprotective agent with unique mechanisms of action," Neurologist 13(5): 272-293 (2007); Shin et al., "Neuropsychotoxic and neuroprotective potentials of dextromethorphan and its analogs," J. Pharmacol. Sci. 116(2): 137-48 (2011).

In most subjects, there is extensive first pass metabolism of DM, and it is generally assumed that the antitussive activity is primarily due to the primary metabolite, dextrorphan. Silvasti et al., "Pharmacokinetics of dextromethorphan and dextrorphan: a single dose comparison of three preparations in human volunteers," Int. J. Clin. Pharmacol. Ther. Toxicol., 9:493-497 (1987). As a result of genetic polymorphisms of the cytochrome P-450 2D6 enzyme, profound variations occur in the rate of DM metabolism. Hildebrand et al., "Determination of dextromethorphan metabolizer phenotype in healthy volunteers," Eur. J. Clin. Pharmacol. 36:315-318 (1989).

So-called "fast metabolizers" constitute about 84% of the population. After a 30 mg dose, plasma levels in fast metabolizers are less than 5 ng/ml four hours post ingestion. "Intermediate metabolizers" constitute about 6.8% of the population, and "poor metabolizers" constitute 5% to 10% of the Caucasian population. After an oral dose of 30 mg, plasma levels in poor metabolizers remain above 5 ng/ml even at 24 hours. Woodworth et al., "The polymorphic metabolism of dextromethorphan," J. Clin. Pharmacol., 27:139-143 (1987); Kupfer et al., "Pharmacogenetics of dextromethorphan O-demethylation in man," Xenobiotica, 16:421-433 (1986). Attempts have been made to generate more-slowly-metabolized analogues of DM by replacing cytochrome P-450 substrate hydrogens with deuterium and fluorine (A. Thomas, U.S. Patent Publication No. 2018/0344727.)

Quinidine, a cardiac drug, became of interest in connection with DM metabolism when it was found to inhibit the liver cytochrome P-450 2D6 enzyme. Inaba et al., "In vitro inhibition studies of two isozymes of human liver cytochrome P-450," Drug Metab. Disp., 13:443-448 (1985). Co-administration of quinidine with DM slows the metabolism of DM effectively enough to prolong the concentration and half-life of DM in circulating blood. Schadel et al., "The pharmacokinetics of dextromethorphan and metabolites in humans: influence of the CYP2D6 phenotype and quinidine inhibition," J. Clin. Psychopharmacol., 15(4):263-269 (1995). Studies in human subjects demonstrated that doses of quinidine (15-30 mg b.i.d.) lower than those customarily prescribed for heart arrhythmia patients could be used to convert "fast metabolizers" into "poor metabolizers", resulting in a regimen that allowed prescribing physicians to achieve predictable blood levels of DM with a combination product incorporating both DM and quinidine. The clinical utility of the regimen depends on whether the desired pharmacological effects are due to DM, dextrorphan, or both, or to secondary metabolites.

During studies on patients suffering from amyotrophic lateral sclerosis, unexpected results began to appear among subjects receiving the DM/quinidine combination. These benefits included sometimes dramatic reductions in a condition which was then commonly referred to as "emotional lability" or "pathological laughing or crying", an impaired ability to control displays of emotion. The term "pseudobulbar affect" (often abbreviated as PBA) had been used in the field since the condition was first described in the 19th century. Efforts to revise this nomenclature have been unsuccessful to date, and the expression "pseudobulbar affect" will be used herein to refer to this condition. After successful clinical trials, a formulation containing dextromethorphan hydrobromide and quinidine sulfate was approved by the FDA for treatment of pseudobulbar affect, and reached the market under the trademark NUEDEXTA™.

Unexpected benefits of the quinidine-DM combination were observed among patients who suffered from other problems as well. Among them are the benefits described in U.S. Pat. No. 6,207,674, "Dextromethorphan and oxidase inhibitor for weaning patients from narcotics and antidepressants"; US Application Publication No. 2007/0191411, "Enhancement of impaired motor and mental functions, using dextromethorphan and oxidase enzyme inhibitor"; US Application Publication No. 2011/0281905, with the same title, focusing on patients suffering from autism; and US Application Publication No. 2012/0172388, with the same title, focusing on patients suffering from Parkinson's disease. The contents of each of the above-cited patents and applications are incorporated herein by reference in their entireties, for all purposes.

Dextromethorphan (DM), and its metabolite dextrorphan, are known to have binding activity to NMDA (N-Methyl-D-aspartate) receptors and sigma receptors. NMDA receptors are normally triggered by glutamate, but it is difficult to devise drug treatments that effectively block the action of glutamate without creating side effects in other parts of the nervous system. For example, a number of competitive NMDA antagonists, such as dizocilpine, ketamine and phencyclidine, are known to potently suppress activity at NMDA receptors, but they are also potent hallucinogens. For this reason, the use of ketamine as a surgical anesthetic is usually accompanied by co-administration of a second drug (typically diazepam) to prevent hallucinations—the "ketamine emergence reaction"—as the patient emerges from anesthesia. Quttainah et al., "Ketamine-Diazepam Protocol for Intravenous Sedation: The Cosmetic Surgery Hospital Experience." Can. J. Plastic Surg., 12:141-143 (2004). Dextromethorphan, by contrast, has mild and tolerable CNS side effects.

Dextromethorphan exerts some of its pharmacologic effects via a different set of neuronal receptors, called sigma-1 receptors. These receptors have not been fully characterized. It is believed that they mediate diverse neuronal activities such as emotional control, motor function, and nociception. A variety of seemingly unrelated drugs bind to the sigma-1 receptor, e.g. fluvoxamine, cocaine, and PCP. The prototypic sigma-1 agonist, pentazocine (Talwin), was prescribed for post-operative analgesia, but was subsequently withdrawn from the market due to its addictive potential and its tendency to provoke hallucinations and disorientation.

When levo- and dextromorphinan pairs are evaluated for their affinities to the mu, kappa, and delta opioid receptors, the N-methyl-d-aspartate (NMDA) channel, and sigma-1 and -2 receptors, it is observed that the levo isomers tend to have higher affinities at the opioid receptors, while the dextro isomers tend to have lower affinities for opioid receptors but comparatively higher affinities for the NMDA and sigma receptors. Sromek et al., "Preliminary pharmacological evaluation of enantiomeric morphinans" *ACS Chemical Neuroscience* 5(2):93-99 (2014). Dextromethorphan, in particular, has substantial affinity for sigma-1 receptors with little liability for tolerance or addiction. The creation of new analogues and derivatives of DM, particularly analogues and derivatives which exhibit the multifaceted, multi-receptor binding activities of DM but with altered affinities for the different receptor types, may therefore lead to new and improved therapeutic utilities.

Accordingly, there is a need for analogues and derivatives of dextromethorphan that exhibit an array of receptor binding activities in proportions that differ from those exhibited by DM.

There is also a need for analogues and derivatives of dextromethorphan which are less susceptible than DM to metabolic degradation, and which can be administered effectively to patients who would benefit from prolonged DM administration, without the need for co-administration of an enzyme inhibitor such as quinidine.

SUMMARY OF THE INVENTION

Compounds of general structures I and II are provided:

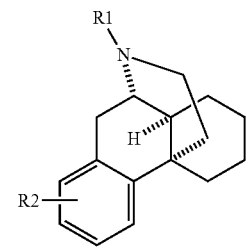

I

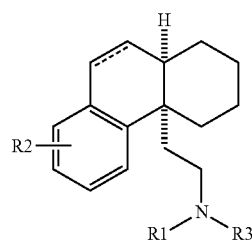

II wherein R1 is H, allyl, C1-C4 alkyl, cyclopropyl, or cyclopropylmethyl, R2 is one or more of halogen, pyridylmethyl, C1-C4 alkyl, or C1-C4 alkoxy. R1 and R2 may optionally substituted with one or more fluorine and/or deuterium atoms. R3 is C1-C4 alkyl, C1-C4 alkenyl, or C1-C4 alkyl substituted with C1-C4 alkoxy or one or more halogens. The compounds are analogues of dextromethorphan (DM) which may have neuronal receptor affinities similar to, and provide the same benefits as, DM. Certain embodiments of structure I are more resistant to metabolism than DM, and are expected to provide more consistent and/or prolonged blood levels. The compounds may have utility as analgesics, and as agents for alleviating the symptoms of pseudobulbar affect. With the exception of structure I where R1 is methyl and R2 is 2,2,2,-trifluoroethyl, the compounds of the invention are novel.

The invention also provides pharmaceutical compositions comprising compounds of structure I or II, and methods of treatment of disease conditions using such compositions.

DETAILED DESCRIPTION OF THE INVENTION

Dextromethorphan (DM) has been used for decades as a safe and non-addictive cough-suppressant, and more recently, it has been found to offer other, additional benefits, if combined with certain other drugs. However, although DM can be highly useful, it does not have consistent effects among different population groups, because of phenotypic variations in how rapidly DM is degraded by the liver enzyme P-450 2D6.

The invention provides compounds of general formulas I and II,

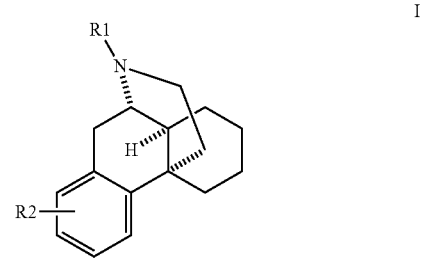

I

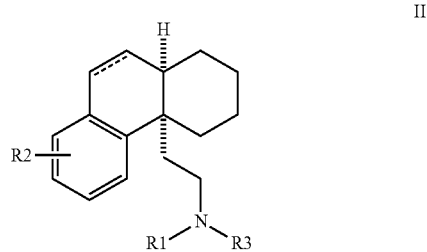

II and pharmaceutical compositions containing them, wherein R1 is H, allyl, C1-C4 alkyl, cyclopropyl, or cyclopropylmethyl; R2 represents one or more of halogen, pyridylmethyl, C1-C4 alkyl, or C1-C4 alkoxy. R1 and R2 are preferably substituted with one or more fluorine and/or deuterium atoms. R3 is C1-C4 alkyl, C1-C4 alkenyl, or C1-C4 alkyl substituted with C1-C4 alkoxy or one or more halogens. Compounds of structures I and II exhibit binding affinities at multiple receptor types that bind dextromethorphan, and certain species exhibit a reduced susceptibility to metabolism by cytochrome P-450.

The Examples below describe the synthetic methods, analytical data, neuronal receptor binding affinities and resistance to degradation by liver enzymes for representative compounds of the invention. Structural formulas for exemplary compounds, and their receptor binding affinities, are shown in the illustrations and tables herein.

The compounds of the invention, having receptor binding profiles similar to DM, are expected to have utility in alleviating the symptoms of pseudobulbar affect, but with an improved duration of action in vivo. Since DM also has efficacy in pain control, the compounds of the invention are expected to have analgesic utility as well. Kim et al., "Comparison of three rodent neuropathic pain models," *Exp. Brain Res.* 113(2):200-206 (1977); Challa, "Surgical animal models of neuropathic pain: Pros and Cons," *Int. J. Neurosci.* (e-pub. June 2014).

Therapeutically effective amounts of the compounds of the invention will vary with the properties of each individual structure, but in general it is expected that unit doses in the range of 1 mg to 1000 mg will be effective when administered orally to human subjects. Depending upon the rates of metabolism and excretion, unit doses may be administered at intervals ranging from 4 to 24 hours.

Included within the scope of the invention are pharmacologically acceptable salts of the compounds described herein. The potency of any candidate salt in emulating the receptor activities of other salts, or of the starting free compounds, can be tested using routine methods to evaluate bioavailability, pharmacokinetics, and receptor binding levels as described below. The physicochemical suitability for manufacturing of the various salts, and polymorphic forms thereof, can likewise be established by routine means.

The term "pharmacologically acceptable" embraces those characteristics which make a drug suitable and practical for manufacturing, distribution, and administration. For example, such compounds must be sufficiently chemically stable under normal storage conditions to have an adequate shelf life, and they must be physiologically and toxicologically acceptable when introduced into the body by a suitable route of administration. Like the reference compound, dextromethorphan free base, the compounds of the invention are alkaline, and they usually will be combined with an acid to create a stable salt that will have good shelf life, and which will not irritate the tongue, mouth, or digestive system when swallowed. Examples of acids which may be employed to form pharmaceutically acceptable salts include but are not limited to inorganic acids such as hydrochloric, sulfuric, nitric, or phosphoric acid, natural organic acids such as maleic, succinic, tartaric, or citric acid, synthetic organic acids such as methanesulfonic, benzenesulfonic, and toluenesulfonic acid, and ion exchange resins such as cross-linked polystyrenesulfonic acid and polymethacrylic acid.

Alternatively, if the substituents which are used to create a particular analog of DM that is of interest give that analog an acidic character, any such acidic analog can be neutralized with a suitable alkaline compound, to create a salt. Pharmaceutically acceptable alkali metal salts or alkaline earth metal salts include, for example, sodium, potassium, calcium and magnesium salts. Ammonium and quaternary ammonium cations and ion exchange resins may also be employed. Any such salts may be prepared by conventional means, which are well-known to chemists who specialize in pharmaceutical formulations.

As used herein, "pharmaceutically acceptable excipient" includes carriers, lubricants, disintegrants, buffers, controlled-release agents, and other additives known in the art of preparing oral, nasal, sublingual, transdermal, or parenteral pharmaceutical compositions. Suitable excipients for solid dosage forms include but are not limited to gelatin, microcrystalline cellulose, sugars, sugar alcohols, cyclodextrins, starches, fatty acid salts of calcium or magnesium. Suitable liquid excipients include but are not limited to water and saline, and alcohols such as ethanol, benzyl alcohol, glycerin and polyethylene glycols. The properties of the formulations may be enhanced by the addition of one or more viscosity enhancers, surfactants, pH modifiers and buffers, preservatives, sweeteners, stability enhancers, coloring agents, suspending agents, granulating agents, coating agents, disintegration aids, emulsifying agents and humectants. Solid dosage forms, such as tablets and capsules, are preferred embodiments.

For purposes of this disclosure, the term "excipient" includes biologically active co-agents such as quinidine, caffeine, bergamottin, and additional neurological receptor agonists and antagonists, which may alter metabolism and pharmacokinetics, or which may alter the balance of receptor types and/or subtypes that are modulated by the compositions of the invention.

Dextromethorphan analogues and derivatives are commonly named in the literature using the Chemical Abstracts nomenclature, as derivatives of (9α,13α,14α)-morphinan.

Dextromethorphan, in this nomenclature, has the systematic name 3-methoxy-17-methyl-(9α,13α,14α)-morphinan. The stereochemical designator "a" at the three chiral centers indicates that each has stereochemistry opposite to that found in the biologically-derived stereoparent, morphinan (III):

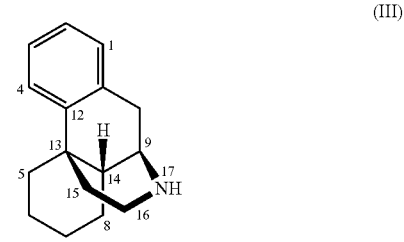

(III)

In IUPAC nomenclature, an alternative systematic name for dextromethorphan is (1S,9S,10S)-4-methoxy-17-methyl-17-azatetracyclo[7.5.3.0$^{1,10}$.0$^{2,7}$]heptadeca-2(7),3,5-triene. The systematic names for the compounds disclosed herein were, in may cases, generated by software. Any errors or discrepancies between a structural drawing and a molecular name should be resolved by reference to, and consistency with, the starting materials and synthetic methods disclosed herein.

EXAMPLES

GENERAL: All temperatures are in degrees Celsius (° C.) and are uncorrected. Reagent grade chemicals and anhydrous solvent were purchased from commercial sources and unless otherwise mentioned, were used without further purification. The names of the products were determined using the naming software included in the electronic lab notebook marketed under the trade name BIOVIA™, or by the MarvinSketch™ software marketed by ChemAxon Kft. Silica gel chromatography was performed on Teledyne ISCO instruments using pre-packaged disposable SiO$_2$ stationary phase columns with eluent flow rate range of 15 to 200 mL/min and UV detection at 254 and 280 nm. Analytical HPLC was performed using an Agilent™ 1100 series instrument equipped with a 190 nm to 300 nm diode array detector. Mass spectra were recorded with a Waters™ SQ detector at 150° C. The mass spectrometer was equipped with an electrospray ion source (ESI) operated in a positive or negative ion mode and was set to scan between m/z 150-750 or m/z 100-2000 with a scan time of 0.2 s. Intermediates were analyzed by HPLC/MS on a Phenomenex™ Kinetex™ EVO C18 (5 µM, 4.6×50 mm) column using a gradient of 5% to 100% of MeCN in H$_2$O (10 mM ammonium formate, pH 3.8) over 2.5 min at 2.2 mL/min for a 3.5 min run (method "A05".) Final products were analyzed by Waters™ UPLC/MS on a BEH C18 (1.7 µM, 2.1×50 mm) column using a gradient of 5% to 100% of ACN in H$_2$O (10 mM ammonium formate, pH 3.8) over 9 min at 0.7 mL/min and hold 100% MeCN 1 min at 0.8 mL/min (method "QC"). $^1$H NMR spectra were recorded on a Bruker™ UltraShield™ 500 MHz/54 mm instrument (BZH 43/500/70B, D221/54-3209). Chemical shifts are referenced to solvent peaks, which in $^1$H NMR appear at 7.26 ppm for CDCl$_3$, 2.50 ppm for DMSO-d6, and 3.31 ppm for CD$_3$OD, and in $^{13}$C NMR appear at 77.16 ppm for CDCl$_3$, 39.52 ppm for DMSO-d6, and 49.00 ppm for CD$_3$OD.

Example 1: Dextrorphan Free Base

Commercially available dextrorphan tartrate (254 mg, 0.622 mmoles) was placed in a 20 ml glass vial, and saturated aqueous sodium bicarbonate (6 ml) was added slowly at 25° C. The reaction mixture was stirred at 25° C. for 20 min to give a white precipitate, which was extracted with dichloromethane (3×20 ml). The combined extracts were dried with anhydrous MgSO4, and the solvent was concentrated to give a solid which was dried in vacuo (0.1 mm Hg) overnight to give free dextrorphan as a white waxy solid (154 mg, 96% yield). Nuclear magnetic resonance (1H-NMR) and liquid chromatography-mass spectrometry (LCMS) results were consistent with published spectra.

Example 2: Synthesis of CNS1

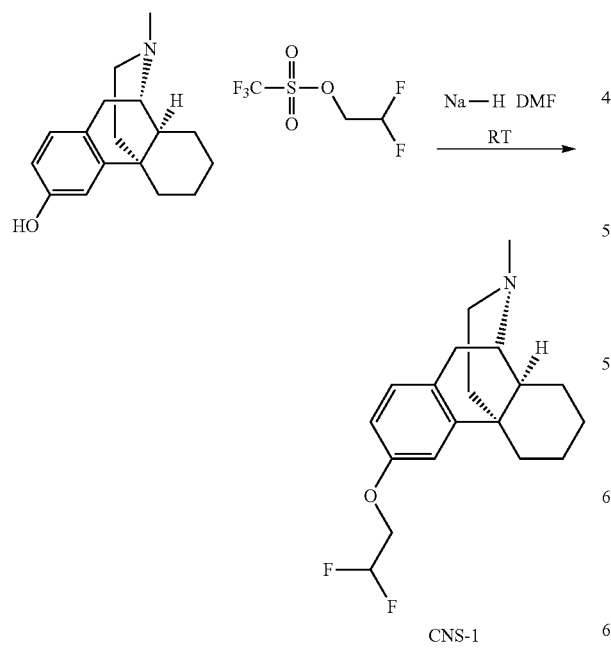

Dextrorphan free base (160 mg, 0.622 mmoles, Example 1) was dissolved in anhydrous DMF (1.24 ml) under an argon atmosphere, sodium hydride (35 mg, 0.815 mmoles) was added, and the reaction mixture was stirred for 20 min at room temperature. The reaction mixture was cooled to 5° C., and 2,2-difluoroethyl triflate (0.091 ml, 0.684 mmoles) was added dropwise.

The reaction mixture was allowed to warm to room temperature, and stirred for 16 hours to give a dark solution. The reaction mixture was diluted with ethyl acetate (30 ml), then washed with H$_2$O (2×8 ml) and brine (8 ml) and dried with MgSO$_4$. The solution was concentrated to give an oil (236 mg) which was dissolved in dichloromethane (200 ml) and purified by dry column gradient flash chromatography (SiO$_2$ chromatography) using a 3.5 cm diameter×3.0 cm height column. The column was dry-packed and the silica equilibrated with (10% 7M ammonia in methanol)/(90% dichloromethane) until the eluent was basic (~30 ml). The material was loaded onto the column and eluted with a step gradient of 7M ammonia/methanol in dichloromethane (10 ml/step.) The percentages of 7M ammonia in methanol were as follows: 1) 0%, 2) 2.5%, 3) 5%, 4) 7.5%, 5) 10%, 6) 10%, and 7) 10%. The product eluted in fractions 5 and 6, which were concentrated to give CNS-1 free base as an oil (120 mg, 60%).

$^1$H NMR (499 MHz, CDCl$_3$) δ 7.04 (dd, J=8.4, 1.0 Hz, 1H), 6.82 (d, J=2.7 Hz, 1H), 6.68 (dd, J=8.4, 2.7 Hz, 1H), 6.08 (tt, J=55.3, 4.2 Hz, 1H), 4.16 (td, J=13.2, 4.1 Hz, 2H), 2.98 (d, J=18.2 Hz, 1H), 2.95 (s, OH), 2.88 (d, J=0.7 Hz, OH), 2.81 (dd, J=5.8, 3.1 Hz, 1H), 2.63-2.53 (m, 1H), 2.43 (ddd, J=11.9, 4.9, 1.9 Hz, 1H), 2.39 (s, 3H), 2.33 (dq, J=13.2, 2.5 Hz, 1H), 2.05 (td, J=12.3, 3.3 Hz, 1H), 1.83 (dt, J=12.8, 3.2 Hz, 1H), 1.74 (td, J=12.7, 4.8 Hz, 1H), 1.69-1.58 (m, 1H), 1.58-1.47 (m, 1H), 1.46-1.19 (m, 5H), 1.10 (qd, J=12.5, 3.8 Hz, 1H).

LCMS: mass calculated for C$_{19}$H$_{25}$F$_2$NO: 321.2; found: 322.3 (M+H)+.

CNS1-free base (120 mg, 0.373 mmol) was dissolved in diethyl ether (2 ml), cooled to 5° C., and 2 M HCl (2.0 ml, 2.0 mmol) in diethyl ether was added dropwise. The resulting gummy solid precipitate was triturated in diethyl ether and dried under vacuum (30 mm Hg) at room temperature and then at high vacuum (0.1 mm Hg) for 30 minutes to give CNS-1 HCl salt as a white foamy solid that was crushed to a hygroscopic powder (96 mg).

$^1$H NMR (499 MHz, DMSO-d6) δ 10.62 (s, 1H), 7.15 (dd, J=8.4, 5.7 Hz, 1H), 7.02-6.77 (m, 2H), 6.37 (tt, J=54.6, 3.6 Hz, 1H), 4.29 (tdd, J=14.8, 5.6, 3.5 Hz, 2H), 3.65-3.49 (m, 1H), 3.23-2.84 (m, 4H), 2.76 (d, J=4.9 Hz, 3H), 2.46-2.30 (m, 1H), 2.22-1.98 (m, 1H), 1.87 (td, J=13.6, 4.6 Hz, 1H), 1.61 (d, J=12.9 Hz, 1H), 1.56-1.20 (m, 5H), 1.20-0.80 (m, 3H).

LCMS: mass calculated for C$_{19}$H$_{25}$F$_2$NO: 321.2; found: 322.3 (M+H)+.

Example 3: Synthesis of CNS2

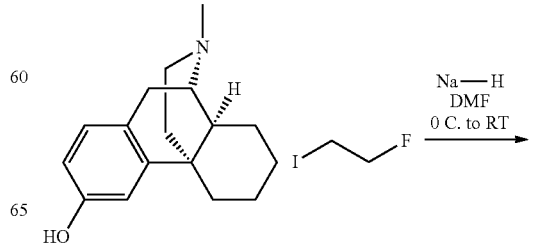

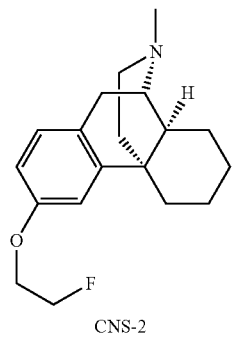

CNS-2

Dextrorphan free base (252 mg, 0.933 mmoles) was dissolved in anhydrous DMF (1.86 ml) and sodium hydride (52 mg, 1.31 mmoles) was added. The reaction mixture was stirred under argon at room temperature for 25 minutes. The turbid solution was cooled to 4° C. and 1-fluoro-2-iodoethane (0.099 ml, 1.212 mmol) was added dropwise. The reaction mixture was allowed to warm to room temperature and stirred under argon for 15 hours to give a suspension, which was diluted with diethyl ether (20 ml) and washed with water (3×4 ml) and brine (4 ml). The organic layer was dried with MgSO4 and solvent was concentrated and further dried under high vacuum to give the titled compound as an oil (280 mg, 98%).

$^1$H NMR (499 MHz, CDCl$_3$) δ 7.03 (d, J=8.3 Hz, 1H), 6.85 (d, J=2.7 Hz, 1H), 6.70 (dd, J=8.4, 2.7 Hz, 1H), 4.75 (dt, J=47.4, 4.2 Hz, 2H), 4.31-4.06 (m, 2H), 2.98 (d, J=18.1 Hz, 1H), 2.81 (dd, J=5.8, 3.2 Hz, 1H), 2.58 (dd, J=18.2, 5.8 Hz, 1H), 2.43 (ddd, J=11.9, 4.9, 1.9 Hz, 1H), 2.40 (s, 3H), 2.37-2.30 (m, 1H), 2.06 (td, J=12.3, 3.3 Hz, 1H), 1.82 (dt, J=12.9, 3.2 Hz, 1H), 1.74 (td, J=12.7, 4.8 Hz, 1H), 1.68-1.58 (m, 1H), 1.51 (dd, J=13.3, 3.5 Hz, 1H), 1.47-1.18 (m, 7H), 1.12 (qd, J=12.5, 3.8 Hz, 1H), 0.92-0.78 (m, 1H).

LCMS: mass calculated for C$_{19}$H$_{26}$FNO: 303.20; found: 304.2 (M+H)+.

A freshly prepared solution of oxalic acid (0.156 M) was prepared by dissolving oxalic acid (420 mg, 4.66 mmoles) in diethyl ether (29.9 ml). CNS2-free base (283 mg, 0.933 mmol) was dissolved in diethyl ether (3.73 ml) to give a 0.25 M solution to which the 0.156 M oxalic acid in diethyl ether (15.0 ml, 2.33 mmol) was added dropwise over 10 min at room temperature using a syringe pump, with stirring, to give a white precipitate. The mixture was stirred for 20 min, the solid was filtered, washed thrice with diethyl ether, air-dried, then dried in vacuo (0.1 mm Hg) for 3 h to give a non-hygroscopic white solid (292 mg, 80%).

$^1$H NMR (499 MHz, dimethyl sulfoxide-d6) δ 7.15 (d, J=8.4 Hz, 1H), 6.98-6.75 (m, 2H), 4.88-4.64 (m, 2H), 4.31-4.14 (m, 4H), 3.53 (d, J=4.4 Hz, 1H), 3.14 (d, J=19.4 Hz, 1H), 3.10-2.92 (m, 2H), 2.81 (s, 3H), 2.47 (d, J=14.3 Hz, 2H), 2.02 (d, J=11.9 Hz, 1H), 1.83 (s, 1H), 1.62 (d, J=12.9 Hz, 1H), 1.57-1.05 (m, 7H), 0.98 (tt, J=13.0, 6.3 Hz, 1H).

LCMS: mass calculated for C$_{19}$H$_{26}$FNO: 303.20; found: 304.2 (M+H)+.

Elemental analysis calculated for C$_{21}$H$_{28}$FNO$_5$ (1:1 oxalate salt): C, 64.11; H, 7.17; N, 3.56. Found: C, 63.86; H, 7.54; N, 3.63.

Example 4: Synthesis of CNS5

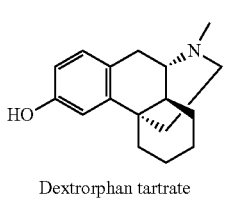 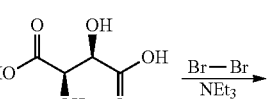

Dextrorphan tartrate

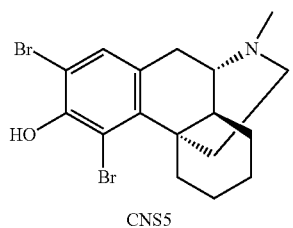

CNS5

Dextrorphan tartrate (500 mg, 1.227 mmol) was suspended in glacial AcOH (6.14 ml), and triethylamine (0.855 ml, 6.14 mmol) was added, resulting in dissolution and a mild exotherm. The reaction mixture was cooled to room temperature, and 2.0 M bromine in acetic acid (1.23 ml, 2.45 mmol) was added dropwise with stirring to give a pale yellow solution which was stirred for 2 hr, after which LCMS showed absence of starting material. The reaction mixture was cooled to 5° C., and 30% aqueous NH$_4$OH (15 ml) was added dropwise with stirring to give a white suspension which was stirred for several hours. The solid was filtered, washed with water 3 times, and dried in vacuo (0.1 mm Hg) to give (1S,9S,10S)-3,5-dibromo-4-hydroxy-17-methyl-17-azatetracyclo[7.5.3.0$^{1,10}$.0$^{2,7}$]heptadeca-2(7),3,5-triene (CNS-5) free base, as a white solid (485 mg, 95%).

$^1$H NMR (dimethyl sulfoxide-d6) δ 7.34 (s, 1), 3.85 (bs, 1), 3.83 (bs, 1), 2.89 (m, 1), 2.66 (m, 2), 2.39 (m, 1), 2.23 (s, 3), 1.89 (m, 2), 1.72 (m, 1), 1.55 (m, 1), 1.47 (m, 2), 1.35 (m, 2), 1.10 (m, 1), 0.95 (m, 2).

LCMS calc for C$_{17}$H$_{21}$Br$_2$NO: 413.00. Found: 414, 416 (M+H)$^+$.

CNS-5 free base (485 mg, 1.168 mmol) was dissolved in dichloromethane (20 ml) to give an amber solution, which was cooled to 5° C. TFA (0.450 ml, 5.84 mmol) was added dropwise at 5° C. with stirring, and the reaction mixture was allowed to warm to room temperature. The reaction mixture was diluted with toluene (20 ml), the solvent was concentrated at 25° C. to a small volume (10 ml) which was co-evaporated with toluene (20 ml) again at 25° C. to give an oil which was dried in vacuo (0.1 mm Hg) to give the TFA salt as an oil (0.618 mg, 95%).

$^1$H NMR (499 MHz, dimethyl sulfoxide-d6) δ 9.83 (s, 1H), 9.65 (s, 1H), 7.45 (d, J=14.2 Hz, 1H), 3.86 (dd, J=34.0, 14.3 Hz, 5H), 3.59 (s, 1H), 3.17 (d, J=5.6 Hz, 3H), 3.06-2.93 (m, 1H), 2.80 (d, J=4.5 Hz, 3H), 2.09 (d, J=14.3 Hz, 1H), 1.95 (dt, J=12.7, 3.3 Hz, 1H), 1.75-0.76 (m, 15H).

LCMS calc for C$_{17}$H$_{21}$Br$_2$NO: 413.00. Found: 414, 416 (M+H)$^+$.

Example 5: Synthesis of CNS6

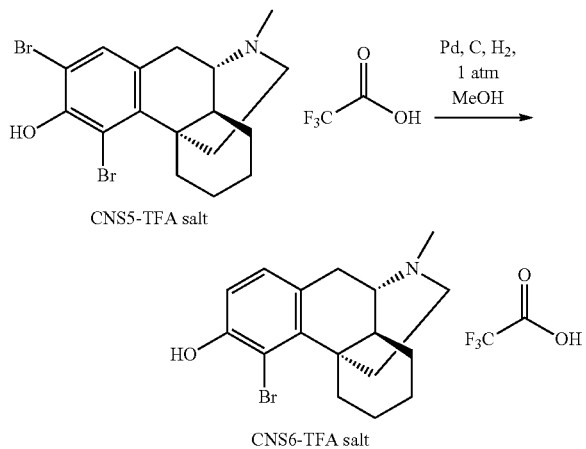

(1S,9S,10S)-3,5-dibromo-4-hydroxy-17-methyl-17-azatetracyclo[7.5.3.0$^{1,10}$.0$^{2,7}$]-heptadeca-2(7),3,5-triene (CNS-5) (618 mg, 1.17 mmol) was dissolved in MeOH (12 ml). Pd/C, 10 wt %, (618 mg) (wet, Degussa type E101 NE/W) was added, and the reaction mixture was stirred under hydrogen (1 atm, balloon) for 2.5 hr. The balloon was recharged with hydrogen, and the mixture was stirred for an additional hour, then filtered through a bed of Celite™ diatomaceous earth. The bed was washed with MeOH and the filtrate was concentrated in vacuo at 35° C. to give (1S,9S,10S)-3-bromo-4-hydroxy-17-methyl-17-azatetracyclo[7.5.3.0$^{1,10}$.0$^{2,7}$]-heptadeca-2(7),3,5-triene trifluoroacetate salt as a beige foam (526 mg, 95%).

1H NMR (dimethyl sulfoxide-d$_6$) δ 7.05 (d, 1, J=8.0 Hz), 6.88 (d, 1, J=8.0 Hz), 3.98 (bs, 1), 3.96 (bs, 1),3.16 (s, 3), 3.12 (d, 1, J=3.5 Hz), 3.00 (d, 1, J=3.5 Hz), 2.79 (d, 2, J=4.5 Hz), 2.08 (d, 1, J=14 Hz), 1.93 (d, 1, J=12 Hz), 1.70 (m, 1), 1.62 (m, 1), 1.53 (m, 1), 1.47 (m, 1), 1.38 (m, 1), 1.03 (m, 3).

LCMS calc for C$_{17}$H$_{22}$BrNO: 335.09. Found: 336, 338 (M+H)$^+$.

Example 6: Synthesis of CNS6-A1

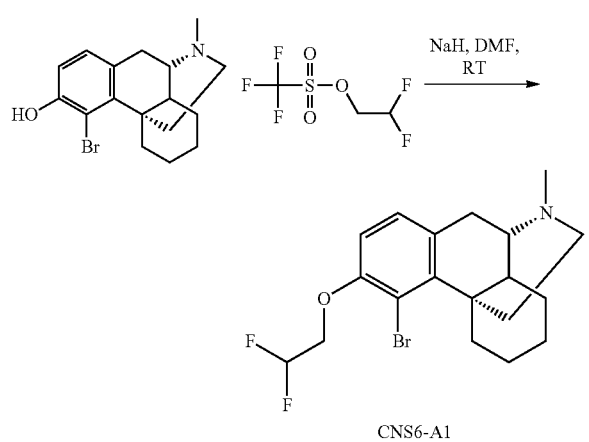

CNS-6 (180 mg, 0.535 mmol) free base was dissolved in anhydrous DMF (1.1 ml) under argon, sodium hydride (25.7 mg, 0.642 mmol) was added, and the mixture was stirred until no more hydrogen gas was evolved. The reaction mixture was cooled to 5° C. and 2,2-difluoroethyl triflate (0.079 ml, 0.589 mmol) was added dropwise. The reaction mixture was allowed to warm to 25° C. in the ice bath and stirred under argon for 16 hours. The mixture was diluted with 30 ml ethyl acetate, washed with two 8 ml portions of H$_2$O and 8 ml of saturated sodium chloride, and then dried over MgSO$_4$. The solvent was evaporated to give 317 mg of an oil, which was dissolved in dichloromethane (4 ml) and purified by SiO$_2$ chromatography using dichloromethane-7M ammonia in methanol to give CNS6-A1 free base as an oil (129 mg, 60%).

$^1$H NMR (499 MHz, CDCl$_3$) δ 7.08 (d, J=8.4 Hz, 1H), 6.77 (d, J=8.3 Hz, 1H), 6.16 (tt, J=55.2, 4.2 Hz, 1H), 4.32-4.10 (m, 2H), 4.02 (ddd, J=11.7, 4.0, 1.6 Hz, 1H), 3.50 (d, J=3.2 Hz, 1H), 2.99 (dd, J=19.8, 2.4 Hz, 1H), 2.88-2.78 (m, 2H), 2.60-2.49 (m, 1H), 2.41 (s, 3H), 2.16-2.03 (m, 2H), 1.90 (d, J=12.7 Hz, 1H), 1.66 (ddd, J=16.3, 10.6, 3.1 Hz, 2H), 1.60-1.51 (m, 1H), 1.50-1.36 (m, 2H), 1.32-1.16 (m, 2H), 1.14-1.03 (m, 2H).

LCMS: mass calculated for C$_{19}$H$_{24}$BrF$_2$NO: 399.10; found: 400, 402 (M+H)+.

The above procedure for preparation of oxalate salts (Example 3) was used to give CNS6-A1 oxalate as a white solid (124 mg, 78%).

$^1$H NMR (499 MHz, dimethyl sulfoxide-d6) δ 7.23 (d, J=8.6 Hz, 1H), 7.11 (d, J=8.6 Hz, 1H), 6.40 (tt, J=54.4, 3.6 Hz, 1H), 4.47-4.24 (m, 3H), 3.95 (d, J=14.4 Hz, 2H), 3.50 (s, 2H), 3.38 (q, J=7.0 Hz, 2H), 3.28-2.98 (m, 4H), 2.77 (s, 3H), 2.16-1.93 (m, 2H), 1.75 (s, 1H), 1.66-1.29 (m, 4H), 1.24 (s, 1H), 1.16-1.01 (m, 2H), 0.95 (t, J=13.1 Hz, 1H).

LCMS: mass calculated for C$_{19}$H$_{24}$BrF$_2$NO: 399.10; found: 400, 402 (M+H)$^+$.

Example 7: Synthesis of CNS6-A2 Free Base and Oxalate Salt

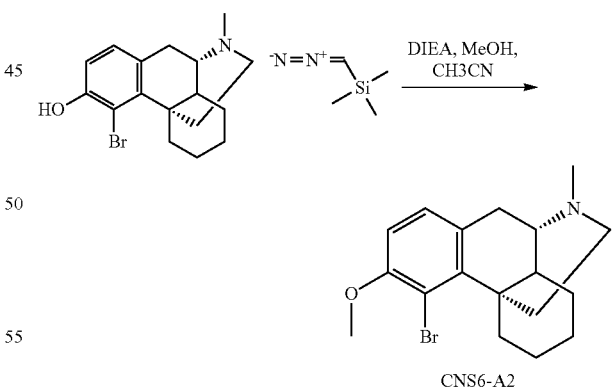

CNS6 free base (180 mg, 0.535 mmol) was suspended in CH$_3$CN (8 ml) and MeOH (0.8 ml), and diisopropylethylamine (DIEA) (0.131 ml, 0.749 mmol) was added to give a suspension to which trimethylsilyldiazomethane (0.375 ml, 0.749 mmol) was added at room temperature. After stirring at room temperature for 16 hr, additional DIEA (0.047 ml, 0.268 mmol) and trimethylsilyldiazomethane (0.134 ml, 0.27 mmol) were added dropwise. After 2 hr the reaction mixture was diluted with toluene (10 ml), and the solution was concentrated at 25° C. in vacuo (30 mm, then 1 mm Hg) to give an oil, which was dissolved in dichloromethane (4 ml). SiO$_2$ chromatography using dichloromethane-7M ammonia/methanol provided CNS6-A2 free base as an oil after evaporation (103 mg, 55%).

$^1$H NMR (499 MHz, CDCl$_3$) δ 7.06 (dt, J=8.2, 0.9 Hz, 1H), 6.75 (d, J=8.4 Hz, 1H), 4.10-3.96 (m, 1H), 3.87 (s, 3H), 3.49 (d, J=5.1 Hz, 1H), 2.97 (d, J=18.8 Hz, 1H), 2.82 (t, J=6.9 Hz, 2H), 2.53 (d, J=11.6 Hz, 1H), 2.40 (s, 3H), 2.16-2.02 (m, 2H), 1.88 (d, J=12.7 Hz, 1H), 1.71-1.58 (m, 3H), 1.48-1.36 (m, 2H), 1.30-1.16 (m, 2H), 1.16-1.03 (m, 2H).

LCMS: mass calculated for C$_{18}$H$_{24}$BrNO: 349.10; found: 350, 352 (M+H)$^+$.

The procedure for preparation of oxalate salts was used to give CNS6-A2 oxalate as a white solid (119 mg, 94%).

1H NMR (499 MHz, dimethyl sulfoxide-d6) δ 7.22 (d, J=8.5 Hz, 1H), 7.04 (d, J=8.4 Hz, 1H), 3.96 (d, J=14.0 Hz, 3H), 3.82 (s, 4H), 3.50 (s, 2H), 3.43-3.34 (m, 1H), 3.13 (d, J=27.0 Hz, 3H), 2.78 (s, 3H), 2.68-2.60 (m, 1H), 2.14-1.92 (m, 2H), 1.73 (s, 1H), 1.48 (ddd, J=69.6, 40.8, 12.9 Hz, 4H), 1.24 (s, 2H), 1.17-1.02 (m, 2H), 0.95 (t, J=13.1 Hz, 1H).

LCMS: mass calculated for C$_{18}$H$_{24}$BrNO: 349.10; found: 350, 352 (M+H)+.

Example 8: Synthesis of CNS1-A8

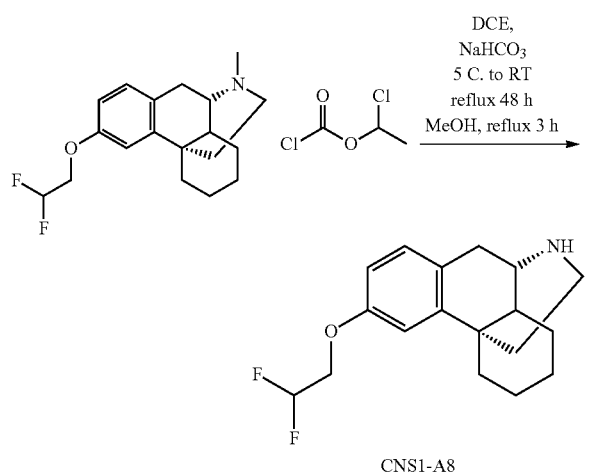

CNS1-A8

CNS1 (386 mg, 1.20 mmol) was dissolved in anhydrous dichloroethane (4.8 ml), NaHCO$_3$ (151 mg, 1.80 mmol) was added, the reaction mixture was cooled to 4° C., and 1-chloroethyl chloroformate (1.13 ml, 10.3 mmol) was added dropwise while stirring. The reaction mixture was allowed to warm to RT, then heated at reflux temperature under argon for 70 h after which most of the solvent had been lost to give a dark mixture. The reaction mixture was filtered through paper, the solids were washed with dichloromethane thrice, and the solvent was concentrated to give a dark oil which was dissolved in MeOH (20 ml). The reaction mixture was heated at reflux temperature for 16 h, the solvent was concentrated to give a dark residue which was dissolved in dichloromethane (4 ml) and purified by SiO$_2$ chromatography using dichloromethane-7M ammonia in methanol to give CNS1-A8 free base as an oil (66 mg) with approximately 90% purity by LCMS.

LCMS: mass calculated for C$_{18}$H$_{23}$F$_2$NO: 307.17; found: 308 (M+H)+.

CNS1-A8 (66 mg, 0.22 mmol, approximately 90% purity) was mostly dissolved in diethyl ether (14 ml) to give a turbid solution which was filtered through a 0.45 um filter disk (2 cm i.d.) to give a solution. The general procedure for preparation of oxalate salts was used to give a gum. The supernatant was carefully decanted off, the gum was washed with diethyl ether twice by decantation to give a residue which was dried in vacuo (0.1 mm Hg) to give CNS1-A8 oxalate as a hygroscopic solid (83 mg, 97%).

$^1$H NMR (499 MHz, Methanol-d4) δ 7.18 (d, J=8.4 Hz, 1H), 6.97 (d, J=2.7 Hz, 1H), 6.90 (dd, J=8.5, 2.7 Hz, 1H), 6.15 (tt, J=55.0, 3.8 Hz, 1H), 4.22 (tdd, J=13.8, 3.8, 2.2 Hz, 2H), 3.69 (dd, J=6.3, 3.2 Hz, 1H), 3.49 (q, J=7.1 Hz, 1H), 3.11 (dd, J=13.3, 4.1 Hz, 1H), 2.96 (d, J=19.0 Hz, 1H), 2.73 (td, J=13.4, 3.7 Hz, 1H), 2.50 (d, J=13.9 Hz, 1H), 1.94 (d, J=12.5 Hz, 1H), 1.82 (td, J=13.8, 4.7 Hz, 1H), 1.72 (d, J=13.2 Hz, 1H), 1.61 (d, J=14.1 Hz, 2H), 1.53 (d, J=13.7 Hz, 1H), 1.50-1.39 (m, 2H), 1.39-1.26 (m, 2H), 1.19 (dt, J=11.0, 7.0 Hz, 1H), 1.11 (qd, J=12.8, 3.9 Hz, 1H).

LCMS: 96% purity; mass calculated for C$_{18}$H$_{23}$F$_2$NO: 307.17; found: 308 (M+H)$^+$.

Example 9: Synthesis of CNS4

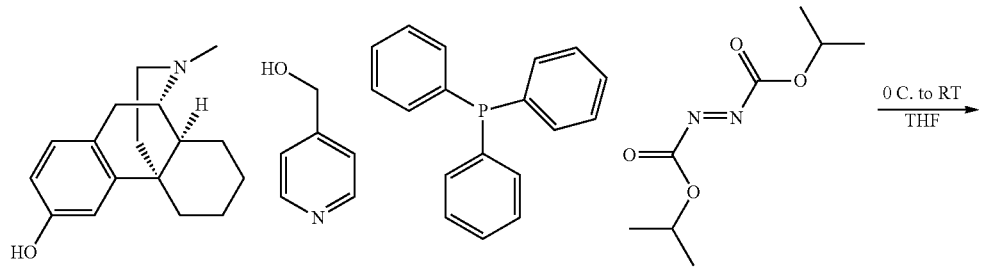

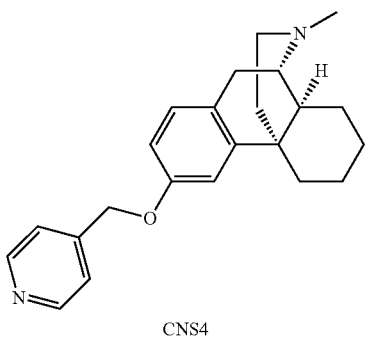

CNS4

Dextrorphan free base (314 mg, 1.22 mmol), pyridin-4-yl-methanol (133 mg, 1.22 mmol) and triphenylphosphine (416 mg, 1.59 mmol) were dissolved in anhydrous tetrahydrofuran (3.7 ml), cooled to 0° C., and diisopropyl azodicarboxylate (0.312 ml, 1.59 mmol) was added dropwise with stirring to give an amber solution. The solution was allowed to warm to room temperature, stirred for 3 hr, and concentrated to give an oil which was purified by $SiO_2$ chromatography (dichloromethane-MeOH) to give CNS4 free base as an oil (107 mg, 25%).

1H NMR (499 MHz, $CDCl_3$) δ 8.67-8.52 (m, 2H), 7.42-7.31 (m, 2H), 7.04 (d, J=8.4 Hz, 1H), 6.85 (d, J=2.6 Hz, 1H), 6.74 (dd, J=8.4, 2.6 Hz, 1H), 5.06 (s, 2H), 3.48 (s, OH), 2.99 (d, J=18.2 Hz, 1H), 2.87 (t, J=4.4 Hz, 1H), 2.64 (dd, J=18.3, 5.8 Hz, 1H), 2.56-2.47 (m, 1H), 2.44 (s, 3H), 2.36-2.25 (m, 1H), 2.13 (td, J=12.4, 3.3 Hz, 1H), 1.89 (dd, J=9.7, 6.4 Hz, 1H), 1.80 (td, J=12.7, 4.8 Hz, 1H), 1.63 (dt, J=12.7, 3.3 Hz, 1H), 1.48 (d, J=4.2 Hz, 1H), 1.46-1.36 (m, 2H), 1.33 (dt, J=12.9, 3.3 Hz, 2H), 1.28-1.17 (m, 2H), 1.17-1.03 (m, 1H).

LCMS: mass calculated for $C_{23}H_{28}N_2O$: 348.22; found: 349.5 $(M+H)^+$.

CNS4 free base (107 mg, 0.307 mmol) was dissolved in EtOH (3.0 ml), 0.156 M oxalic acid in diethyl ether (9.9 ml, 1.54 mmol) was added dropwise over 10 min using a syringe pump at RT while stirring to give a hygroscopic precipitate. The supernatant was decanted off, diethyl ether (30 ml) was added to the residue, the mixture was stirred for 5 min, and the supernatant was decanted off again. This trituration with diethyl ether (30 ml) was repeated again and the diethyl ether was decanted off to give a solid which was dried in vacuo (0.1 mm Hg) for 3 hr to give the oxalate salt as a pink hygroscopic powder (115 mg, 87%).

$^1$H NMR (499 MHz, DMSO-d6) δ 8.63-8.48 (m, 2H), 7.50-7.35 (m, 2H), 7.14 (d, J=8.3 Hz, 1H), 6.97-6.82 (m, 2H), 5.25-5.06 (m, 2H), 3.41 (dq, J=28.5, 7.0 Hz, 1H), 3.12 (s, 2H), 2.97 (d, J=20.6 Hz, 1H), 2.88-2.72 (m, 2H), 2.41 (d, J=14.3 Hz, 2H), 1.99 (s, 1H), 1.79 (s, 1H), 1.58 (d, J=12.9 Hz, 1H), 1.45 (d, J=14.3 Hz, 3H), 1.28 (s, 2H), 1.15-0.82 (m, 3H).

LCMS: mass calculated for $C_{23}H_{28}N_2O$: 348.22; found: 349 $(M+H)^+$.

Example 10: Synthesis of CNS7M

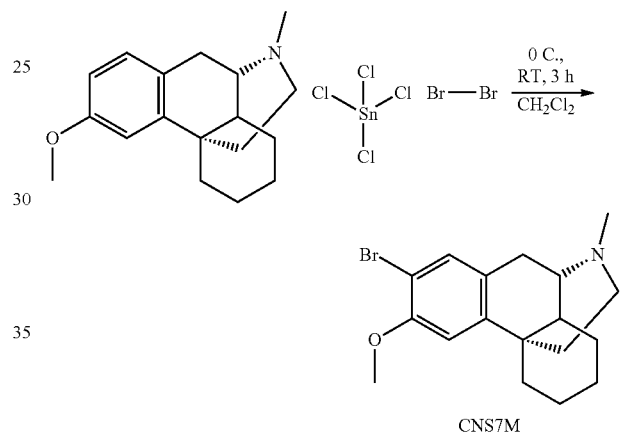

CNS7M

Dextromethorphan free base (248 mg, 0.914 mmol) was dissolved in anhydrous dichloromethane (9 ml), the solution was cooled to 4° C. under argon, and 1.0 M $SnCl_4$ in heptane (3.73 ml, 3.73 mmol) was added to give a slightly turbid solution. Bromine (0.106 ml, 2.05 mmol) was added dropwise at 4° C., the reaction mixture was allowed to warm to RT to give an orange suspension which was stirred at RT for 8 h after which it was poured into sat'd. aqueous $NaHCO_3$ (10 ml) and ice with stirring. Additional sat'd aqueous $NaHCO_3$ (10 ml) was added to pH 8, to give a copious white suspension which was extracted with dichloromethane (100 ml). The organic layer was dried with $MgSO_4$, the solvent was concentrated to give a residue which was dissolved in dichloromethane (5 ml) and purified by $SiO_2$ chromatography using dichloromethane-7M ammonia in methanol to give the titled compound as an oil (230 mg, 71%).

$^1$H NMR (499 MHz, $CDCl_3$) δ 7.28 (s, 1H), 6.76 (s, 1H), 3.86 (s, 3H), 2.95 (d, J=18.2 Hz, 1H), 2.79 (dd, J=5.8, 3.1 Hz, 1H), 2.56 (dd, J=18.2, 5.8 Hz, 1H), 2.44 (ddd, J=12.0, 5.0, 1.8 Hz, 1H), 2.38 (s, 3H), 2.36-2.29 (m, 1H), 2.06 (td, J=12.3, 3.3 Hz, 1H), 1.82 (dt, J=12.9, 3.2 Hz, 1H), 1.74 (td, J=12.6, 4.8 Hz, 2H), 1.69-1.61 (m, 3H), 1.58-1.50 (m, 2H), 1.45-1.20 (m, 7H), 1.10 (qd, J=12.5, 3.7 Hz, 1H).

LCMS: mass calculated for $C_{18}H_{24}BrNO$: 349.10; found: 350, 352 $(M+H)^+$.

Example 11: NDDX Free Base and Oxalate Salt

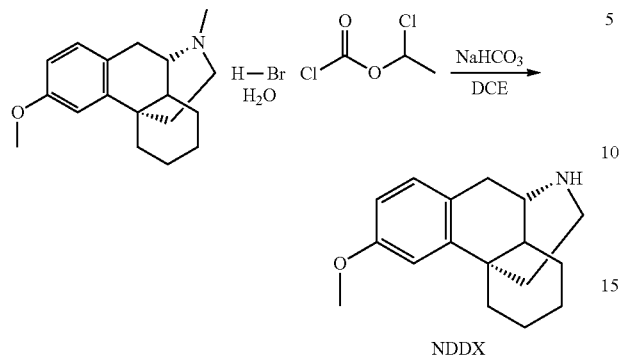

NDDX ("NDDX" is a term used in the art to refer to N-desmethyl dextromethorphan.) Water was removed from dextromethorphan.H$_2$O.HBr (715 mg, 1.93 mmol) by azeotropic distillation with toluene (3×10 ml) to leave a white solid, which was suspended in dichloroethane (DCE, 7.72 ml). NaHCO$_3$ (568 mg, 6.76 mmol) was added, the mixture was cooled to 4° C., and 1-chloroethyl chloroformate (1.81 ml, 16.6 mmol) was added dropwise. The reaction mixture was allowed to warm to RT, then refluxed under argon for 24 h. Additional NaHCO$_3$ (324 mg, 3.86 mmol) was added, and 1-chloroethyl chloroformate (0.210 ml, 1.93 mmol) was added dropwise with stirring. The reaction mixture was refluxed under argon for an additional 16 hr. The solids were filtered off and washed with dichloromethane. The filtrate was concentrated to an oil which was dissolved in MeOH (19 ml), to give a solution which was heated at reflux temperature for 16 h. The solvent was concentrated to give a solid which was partitioned between aqueous 1 N NaOH (8 ml) and diethyl ether (40 ml) (shaken vigorously until all solids dissolved), the organic layer was washed with distilled H$_2$O (8 ml×3), brine (8 ml), dried with MgSO$_4$, and the solvent was removed in vacuo to give NDDX as an amber oil (466 mg, 93%).

$^1$H NMR (499 MHz, CDCl$_3$) δ 7.03 (dt, J=8.4, 1.0 Hz, 1H), 6.80 (d, J=2.6 Hz, 1H), 6.70 (dd, J=8.4, 2.6 Hz, 1H), 3.79 (s, 3H), 3.48 (q, J=7.0 Hz, 1H), 3.11 (ddd, J=17.7, 6.2, 1.1 Hz, 1H), 3.04 (dd, J=6.3, 3.2 Hz, 1H), 2.77-2.55 (m, 3H), 2.30 (dt, J=11.9, 2.3 Hz, 1H), 1.81-1.68 (m, 3H), 1.64 (ddd, J=12.5, 4.4, 2.2 Hz, 1H), 1.61-1.45 (m, 2H), 1.44-1.24 (m, 6H), 1.21 (t, J=7.0 Hz, 1H), 1.05 (qd, J=13.3, 12.6, 3.6 Hz, 1H).

LCMS: mass calculated for C$_{17}$H$_{23}$N$_0$: 257.18; found: 258 (M+H)$^+$.

NDDX free base (258 mg, 1.00 mmol) was dissolved in diethyl ether (4.0 ml), and 0.156 M oxalic acid in diethyl ether (16 ml, 2.5 mmol) was added dropwise over 10 min while stirring to give a beige solid which became a gum. The supernatant was decanted, the gum was triturated with diethyl ether (20 ml) by pulverizing the residue in diethyl ether to give a solid which was filtered, washed with diethyl ether thrice, and dried in vacuo (0.1 mm Hg) to give the titled compound as a hygroscopic solid (259 mg, 75%).

1H NMR (499 MHz, dimethyl sulfoxide-d6) δ 7.13 (d, J=8.5 Hz, 1H), 6.84 (d, J=2.5 Hz, 1H), 6.81 (dd, J=8.5, Hz, 1H), 3.73 (s, 3H), 3.61 (bs, 1H), 3.13-2.9 (m, 3H), 2.4 (m, 2H), 1.9 (bd, 1H), 1.7 (m, 1H), 1.6 (m, 1H), 1.45 (m, 3H), 1.3 (m, 2H), 1.15 (m, 1H), 0.9 (m, 1H).

LCMS: mass calculated for C$_{17}$H$_{23}$N$_0$: 257.18; found: 258 (M+H)$^+$.

Example 12: Synthesis of CNS10

NDDX free base (237 mg, 0.808 mmol) was dissolved in diethyl ether (8 ml), and 1.0 M HCl in diethyl ether (4.0 ml, 4.0 mmol) was added dropwise at RT with stirring. The solvent was removed in vacuo to leave a white solid (262 mg), which was dissolved in MeOH. Pyridine-3-carbaldehyde (0.0913 ml, 0.970 mmol), sodium cyanoborohydride (33.9 mg, 0.539 mmol), and bromocresol green (1 mg) were added at RT to give a blue-green solution which was stirred at RT for 48 hr. Conc. aqueous HCl (0.20 ml) was added at RT to pH 1, and the solvent was removed. The residue was dissolved in distilled H$_2$O (9 ml) to give a turbid solution which was extracted with diethyl ether (3×8 ml). The aqueous layer was basified with solid NaOH (4 pellets) to pH 12, extracted with diethyl ether twice (20 ml, 10 ml), and the organic extracts were dried with MgSO$_4$. The solvent was concentrated to give an oil which was dissolved in dichloromethane (2 ml) and purified by SiO$_2$ chromatography using dichloromethane-MeOH to give CNS10 free base as an oil (97 mg, 34%, 94% purity by LCMS).

$^1$H NMR (499 MHz, CDCl$_3$) δ7.70 (d, J=8.0 Hz, 1H), 7.06 (d, J=8.5 Hz, 1H), 6.81 (d, J=2.5 Hz, 1H), 6.71 (dd, J=8.5, 2.5 Hz, 1H), 3.73 (d, J=13.5 Hz, 1H), 3.59 (d, J=13.5 Hz, 1H), 3.01 (d, J=18.0 Hz, 1H), 2.82 (m, 1H), 2.64 (m, 1H), 2.38 (m, 2H), 2.13 (m, 1H), 1.85 (m, 1H), 1.61 (m, 2H), 1.51 (m, 1H), 1.31 (m, 6H), 1.09 (m, 1H).

LCMS: mass calculated for C$_{23}$H$_{28}$N$_2$O: 348.22; found: 349 (M+H)$^+$.

CNS10 free base (141 mg, 0.405 mmol) was dissolved in EtOH (2.0 ml), 0.156 M oxalic acid in diethyl ether (7.78 ml, 1.21 mmol) was added dropwise over 10 min using a syringe pump at RT while stirring to give a fine suspension. The solvent was removed to give a residue which was triturated with diethyl ether (20 ml) by pulverizing the residue under diethyl ether to give a beige solid which was filtered, washed with diethyl ether, and dried in vacuo (0.1 mm Hg) for 16 h to give CNS10 oxalate as a hygroscopic beige solid (146 mg, 82%).

$^1$H NMR (499 MHz, dimethyl sulfoxide-d6) δ 8.78-8.70 (m, 1H), 8.63 (dd, J=4.8, 1.4 Hz, 1H), 7.98 (d, J=7.8 Hz, 1H), 7.48 (dd, J=7.8, 4.8 Hz, 1H), 7.22-7.14 (m, 1H), 6.87-6.82 (m, 2H), 4.50-4.37 (m, 2H), 3.74 (s, 3H), 3.45 (d, J=4.9 Hz, 1H), 3.29 (s, 1H), 3.01 (s, 2H), 2.56 (t, J=12.6 Hz, 1H), 2.45 (d, J=13.9 Hz, 1H), 2.07 (s, 1H), 1.86 (s, 1H), 1.64-1.11 (m, 8H), 0.94 (td, J=13.3, 9.6 Hz, 1H).

LCMS: mass calculated for $C_{23}H_{28}N_2O$: 348.22; found: 349 (M+H)$^+$.

Example 13: Synthesis of CNS21

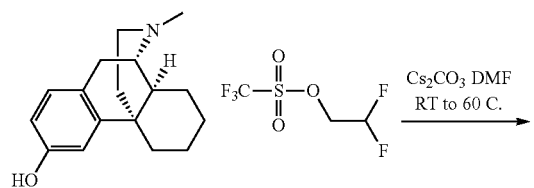

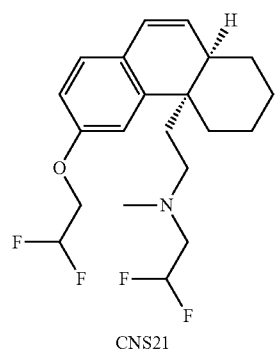

CNS21

Dextrorphan free base (160 mg, 0.622 mmoles) was dissolved in dimethylformamide (DMF, 1.8 ml), diluted with ethyl acetate (30 ml), cesium carbonate (304 mg, 0.933 mmol) was added, and the suspension was stirred for 15 minutes at 25° C. Difluoroethyl triflate (0.091 ml, 147 mg, 0.684 mmoles) was added and the suspension was stirred at room temperature for 16 hours. TLC (silica, 90:10 (dichloromethane/7N $NH_3$ in MeOH) showed the presence of a trace of starting material (Rf 0.45) with the product appearing at Rf 0.9. Using hexane/ethyl acetate (70:30), the starting material had Rf 0.1 and the product had Rf 0.35.

Additional cesium carbonate (101 mg, 0.311 mmole) was added, followed by additional difluoroethyl triflate (0.031 ml), and the mixture was stirred for 24 more hours at 25° C. The reaction mixture was diluted with ethyl acetate (30 ml), and washed with water (18 ml) and brine (2×10 ml). The organic layer was dried with $MgSO_4$, filtered, and the solvent was removed in vacuo (30 mm Hg at 35° C.) to yield 213 mg of crude product as an oil. The product was dissolved in dichloromethane (2.0 ml) and purified by dry column flash chromatography on a 3.5×3.0 cm column using a hexane/ethyl acetate step gradient (0%, 20%, 30%, 40%, 50%, and 60% ethyl acetate). Fraction 3 (30% ethyl acetate) was concentrated to give an oil which was dried under high vacuum (0.1 mm Hg) overnight to give CNS21 free base as an oil (30 mg, 15%).

$^1$H NMR (499 MHz, CDCl$_3$) δ 7.00 (d, J=10.0 Hz, 1H), 6.81 (d, J=2.5 Hz, 1H), 6.68 (dd, J=8, 2.5 Hz, 1H), 6.31 (d, J=9.5 Hz, 1H), 6.09 (tt, $J_{H\text{-}F}$=55 Hz, J=4.0 Hz, 1H), 5.85 (m, 1H), 5.70 (tt, $J_{H\text{-}F}$=56 Hz, J=4.0 Hz, 1H), 4.18 (m, 2H), 2.56 (m, 2H), 2.44 (m, 1H), 2.34 (m, 1H), 2.19 (s, 3H), 2.10 (m, 1H), 2.04 (m, 1H), 1.93 (m, 1H), 1.57 (m, 2H), 1.36 (m, 4H), 0.93 (m, 2H).

LCMS: mass calculated for $C_{21}H_{27}F_4NO$: 385.20; found: 386 (M+H)$^+$.

Example 14: Synthesis of CNS22

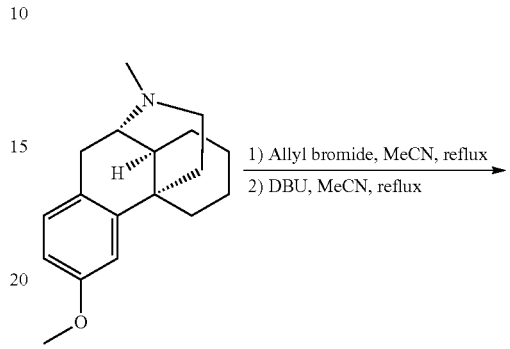

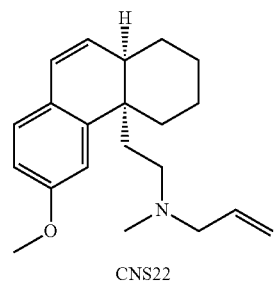

CNS22

Dextrorphan free base (0.731 g, 2.69 mmol) was dissolved in acetonitrile (15.0 ml). Allyl bromide (0.465 ml, 5.39 mmol) was added, the mixture was refluxed for 18 hr, and the solvent was evaporated under reduced pressure. The residue was triturated with hexane, filtered, and dried under high vacuum. The intermediate was dissolved in acetonitrile (15.0 ml), 1,8-diazabicyclo[5.4.0]undec-7-ene (DBU) (0.547 ml, 3.66 mmol) was added, and the mixture was refluxed for 4 hr. The solvent was evaporated under reduced pressure, water (20.0 ml) was added, and the aqueous phase was extracted with EtOAc (3×20 ml). The combined organic phases were washed with brine (20 ml), dried (MgSO4), filtered, and concentrated under reduced pressure. The product was purified by reverse phase chromatography (C18 silica, 54 g cartridge) eluting with a gradient of acetonitrile (50-100%) in pH 10 water to provide the title compound as an oil (232 mg; 28%).

$^1$H NMR (400 MHz, CDCl$_3$) δ 6.97 (d, J=8.2 Hz, 1H), 6.79 (d, J=2.5 Hz, 1H), 6.67 (dd, J=8.2, 2.6 Hz, 1H), 6.29 (d, J=9.5 Hz, 1H), 5.85-5.68 (m, 2H), 5.12-5.01 (m, 2H), 3.81 (s, 3H), 2.92-2.81 (m, 2H), 2.41-2.27 (m, 2H), 2.07 (s, 3H), 2.05-1.90 (m, 3H), 1.62-1.51 (m, 3H), 1.48-1.26 (m, 4H), 1.06-0.92 (m, 1H). m/z (ES+), [M+H]+: 311.8.

Example 15: Synthesis of CNS23

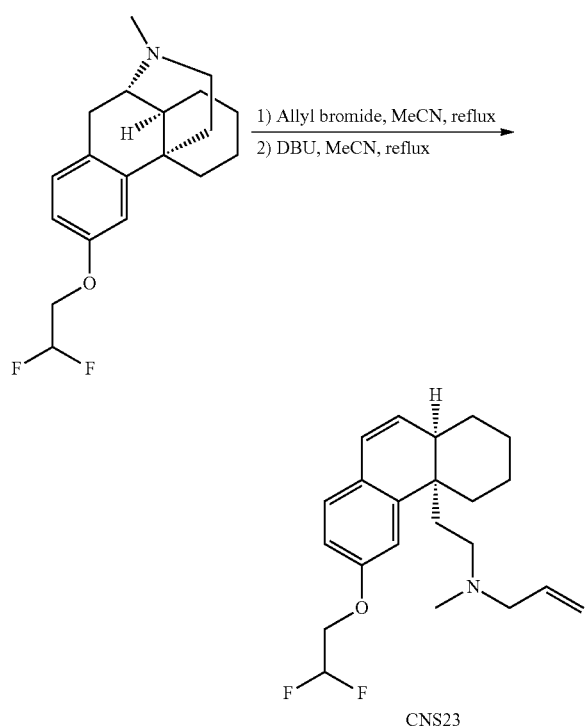

The synthesis follows closely the preparation of CNS22; see Example 14, above, for appropriate quantities and conditions. CNS1 free base (1 equivalent) is dissolved in acetonitrile, allyl bromide (2 equiv.) is added, and the mixture is refluxed for 18 hr. The solvent is evaporated under reduced pressure. The residue is triturated with hexane for 5 min, filtered, and re-dissolved in acetonitrile. DBU (2 equiv.) is added, and the mixture is refluxed for 18 hr. The solvent is evaporated under reduced pressure, water is added, and the mixture is extracted twice with EtOAc. The combined organic phases are washed with brine, dried (MgSO4), filtered, and concentrated in vacuo. The product is purified by revere-phase HPLC (C-18 column), eluting with a gradient of 70-90% acetonitrile in pH 10 water to provide the title compound.

Example 16: Synthesis of CNS25

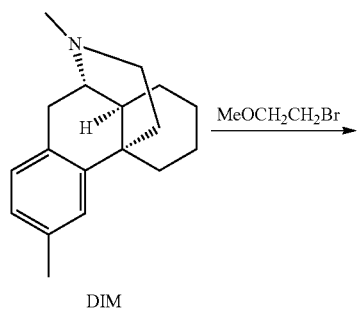

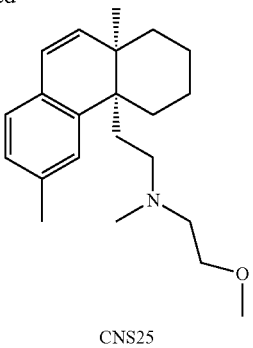

The synthesis follows closely the preparation of CNS22; see the experimental procedure for appropriate quantities and conditions. Dimemorphan (DIM) (1 equivalent) is dissolved in acetonitrile, 2-methoxyethyl bromide (2 equiv.) is added, and the mixture is refluxed for 18 hr. The solvent is evaporated under reduced pressure. The residue is triturated with hexane for 5 min, filtered, and re-dissolved in acetonitrile. DBU (2 equiv.) is added, and the mixture is refluxed for 18 hr. The solvent is evaporated under reduced pressure, water is added, and the mixture is extracted twice with EtOAc. The combined organic phases are washed with brine, dried (MgSO4), filtered, and concentrated in vacuo. The product is purified by revere-phase HPLC (C-18 column), eluting with a gradient of 70-90% acetonitrile in pH 10 water to provide the title compound.

Example 17: Synthesis of CNS26 Free Base

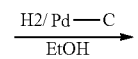

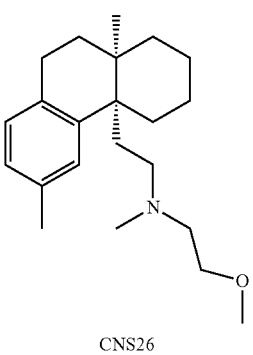

To a solution of CNS25 free base (100 mg) in ethanol (10 ml) is added 10% palladium on carbon catalyst (50 mg). The mixture is stirred overnight under an atmosphere of hydrogen at atmospheric pressure. Filtration and evaporation of solvent leaves the title compound as an oil.

1,1-dideuterio-2,2-difluoroethyl trifluoromethanesulfonate

Difluoroacetic anhydride (10 g, 0.057 mmol) was dissolved in diethyl ether (50 ml) under argon atmosphere. The solution was cooled to −45° C. and NaBD$_4$ (3.6 g, 0.086 mmol) was added in small portions. The reaction mixture was stirred at −45° C. for 30 min and then allowed to warm to room temperature gradually and stirred at room temperature overnight. TLC (EtOAc-Hexane, 1:1) showed a spot at Rf=0.6 (anhydride sits at baseline). The reaction was quenched with conc. HCl (2 ml), the ether solution was dried over MgSO$_4$, and most of the ether was distilled off to leave 2,2-difluoroethan-1,1-d2-1-ol as a clear oil.

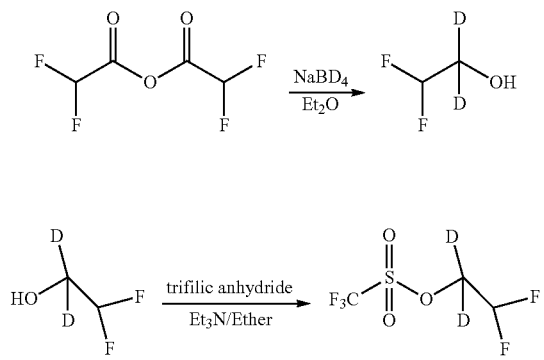

A solution of 2,2-difluoroethan-1,1-d$_2$-1-ol (2 g, 23.8 mmol) in diethyl ether (35 ml) was cooled to −50° C. To this was added trifluoromethanesulfonic anhydride (4.8 ml, 28.5 mmol), followed by triethylamine (3.7 ml, 26.2 mmol). The reaction mixture was stirred at 0° C. for 30 min. 1 N HCl (30 ml) was added and the mixture was extracted with diethyl ether (30 ml×4). The combined organic layer was washed with NaHCO$_3$ (30 ml), then brine (30 ml). The organic phase was dried over Na$_2$SO$_4$, filtered and concentrated under vacuum to give crude 1,1-dideuterio-2,2-difluoroethyl trifluoromethanesulfonate as a liquid.

1,1-dideuterio-2,2-difluoroethyl 4-methylbenzenesulfonate

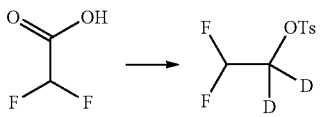 [SMILES: O=C(O)C(F)F ; [2H]C([2H])(OS(=O)(=O)c1ccc(C)cc1)C(F)F]

2,2-difluoroacetic acid (0.950 mL, 15.1 mmol) was slowly added at 0° C. to a mixture of lithium aluminum deuteride (635 mg, 15.1 mmol) in THF (30.0 mL). The mixture was stirred for 2 h at 60° C. then cooled to 20° C. A mixture of wet Na$_2$SO$_4$ and Celite™ was slowly added until bubbling ceased. DCM (100 mL) and Na$_2$SO$_4$ were added and the mixture was stirred for 5 min then filtered through Celite™ washing with DCM (100 mL). 4-Methylbenzenesulfonyl chloride (3.46 g, 18.2 mmol), triethylamine (3.16 mL, 22.7 mmol) and N,N-dimethylpyridin-4-amine (92.5 mg, 0.757 mmol) were added to the filtrate. The mixture was stirred for at 20° C. for 16 h then diluted with saturated aqueous NaHCO$_3$ (150 mL). The combined organic phase was dried (Na$_2$SO$_4$), filtered and concentrated. The residue was purified by silica gel chromatography (80 g cartridge) eluting with hexanes and EtOAc (0-20%) to afford 1,1-dideuterio-2,2-difluoroethyl) 4-methylbenzenesulfonate as an oil (2.28 g, 63% yield). $^1$H NMR (400 MHz, CDCl$_3$) δ 7.81 (d, J=8.4 Hz, 2H), 7.38 (dd, J=8.6, 0.7 Hz, 2H), 5.91 (t, J=54.6 Hz, 1H), 2.47 (s, 3H); LCMS (A05); t$_R$=2.35 m.

Example 18: Synthesis of CNS1-D2

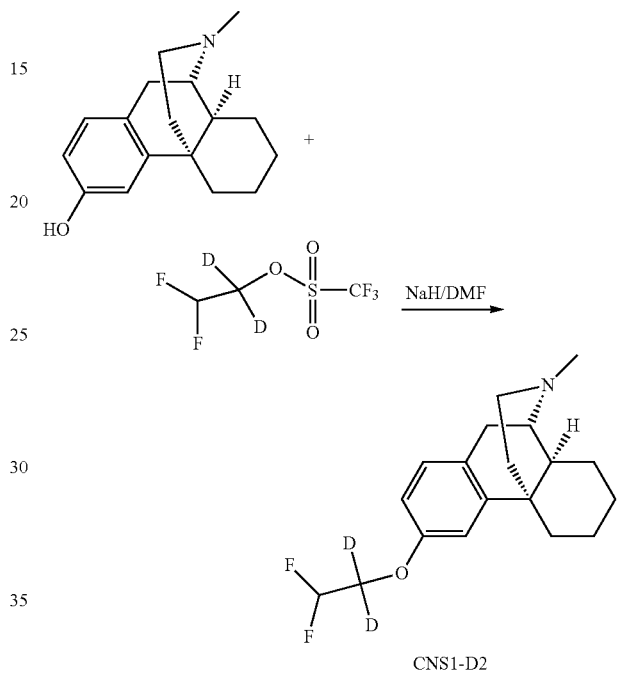

Dextrorphan free base (164 mg, 0.64 mmol) was dissolved in anhydrous DMF (1.25 ml) under argon. To this solution was added sodium hydride (78 mg, 1.92 mmol) and the resulting mixture was stirred at room temperature under argon until evolution of gas stopped (30 min). The reaction was then cooled to 5° C. and 2,2-difluoroethyl-1,1-d$_2$ trifluoromethanesulfonate (0.34 ml, 2.56 mmol) was added dropwise. The reaction mixture was allowed to warm to room temperature and stirred under argon over the weekend. The mixture was diluted with ethyl acetate (30 ml) and washed with water (2×8 ml), then brine (8 ml). The organic layer was dried over Na$_2$SO$_4$, filtered and concentrated to give crude product as light yellow oil (280 mg). The material was purified by dry column gradient flash chromatography on silica gel using a 0 to 10% gradient of 7M NH$_3$/methanol in dichloromethane. Pure fractions (by TLC) were pooled together and solvent was evaporated to dryness to leave ca. 10 mg of (1S,9S,10S)-4-(1,1-dideuterio-2,2-difluoroethoxy)-17-methyl-17-azatetracyclo[7.5.3.0$^{1,10}$.0$^{2,7}$]hepta-deca-2(7),3,5-triene (CNS1-D2 free base) as an oil.

$^1$H NMR (499 MHz, CDCl$_3$) δ 6.96 (d, J=8.2 Hz, 1H), 6.72 (d, J=2.6 Hz, 1H), 6.60 (dd, J=8.2, 2.6 Hz, 1H), 6.1 (t, 1H), 3.01-2.89 (m, 1H), 2.84 (dd, J=5.8, 3.1 Hz, 1H), 2.63 (dd, J=18.2, 5.8 Hz, 1H), 2.56-2.42 (m, 1H), 2.39 (s, 3H), 2.33-2.23 (m, 1H), 2.21-2.02 (m, 2H), 1.86 (dt, J=12.8, 3.2 Hz, 1H), 1.75 (td, J=12.8, 4.8 Hz, 1H), 1.64 (dt, J=12.0, 3.3 Hz, 1H), 1.55-1.44 (m, 1H), 1.44-1.21 (m, 8H).

MS calculated for $C_{19}H_{23}D_2F_2NO$: m/z=323.2; found: Positive ion m/z=324.3 (M+H).

To a solution of CNS1-D2 free base (114 mg, 0.35 mmol) in ether (1.5 ml) was slowly added a freshly prepared ether (3.3 ml) solution of oxalic acid (47.3 mg, 0.53 mmol). A white precipitate formed upon addition of the oxalic acid solution. The resulting mixture was stirred at room temperature for 1 h and stored in a refrigerator over the weekend. The white powder was collected by vacuum filtration, washed with ether (15 ml), and dried under high vacuum for 2 h to give 84.7 mg (59%) of the oxalate salt as a white solid.

$^1$H NMR (499 MHz, DMSO-d6) δ 7.15 (d, J=8.4 Hz, 1H), 6.97-6.82 (m, 2H), 6.36 (t, J=54.5 Hz, 1H), 3.52 (m, 1H), 3.14 (d, J=19.4 Hz, 1H), 3.08-2.87 (m, 2H), 2.79 (s, 3H), 2.03 (d, J=12.4 Hz, 1H), 1.84 (s, 1H), 1.61 (d, J=13.0 Hz, 1H), 1.47 (dt, J=27.7, 13.3 Hz, 3H), 1.38-1.19 (m, 2H), 1.21-1.02 (m, 1H), 1.03-0.82 (m, 1H). $^{13}$C NMR (126 MHz, DMSO) δ 165.00, 157.29, 139.67, 129.81, 127.79, 116.65, 114.76, 113.21, 112.85, 111.99, 59.07, 47.01, 40.65, 40.55, 40.48, 40.38, 40.31, 40.22, 40.05, 39.88, 39.72, 39.55, 36.24, 35.19, 25.90, 25.82, 21.99.

MS calculated for $C_{19}H_{23}D_2F_2NO$: m/z=323.2; found: Positive ion m/z=324.3 (M+H).

Example 19: Synthesis of CNS23-D2

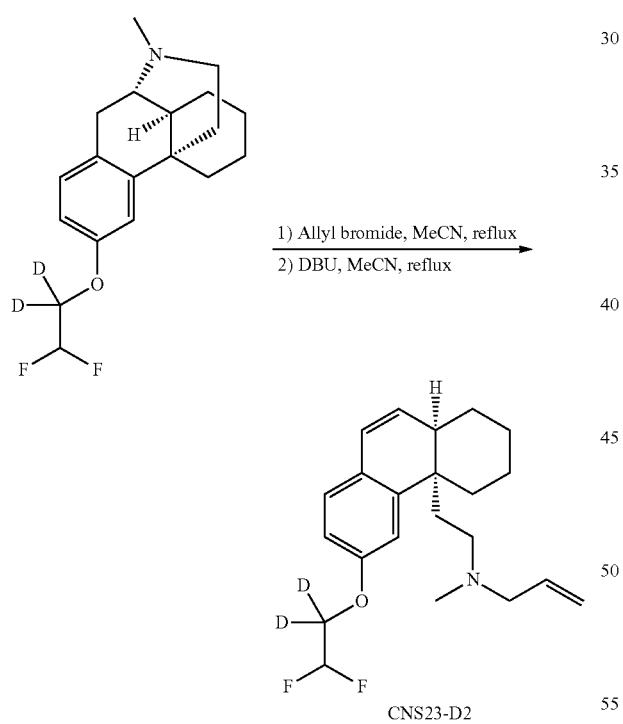

CNS23-D2

(1S,9S,10S)-4-(1,1-dideuterio-2,2-difluoroethoxy)-17-methyl-17-azatetracyclo [7.5.3.0$^{1,10}$.0$^{2,7}$]heptadeca-2(7),3,5-triene (CNS1-D2, 79.7 mg, 0.246 mmol) was dissolved in acetonitrile (2.50 mL). Allyl bromide (42.6 uL, 0.493 mmol) was added, and the mixture was refluxed for 18 hr. The solvent was evaporated under reduced pressure. The residue was triturated with hexane (5.00 mL) for 5 min, filtered, dried under high vacuum, and re-dissolved in acetonitrile (2.50 mL). DBU (55.2 ul, 0.370 mmol) was added, and the mixture was refluxed for 18 hr. The solvent was evaporated under reduced pressure. Water (20.0 mL) was added, and the mixture was extracted with EtOAc (3×20.0 mL). The combined organic phases were washed with brine (20.0 mL), dried (MgSO4), filtered, and concentrated under reduced pressure. The product was purified by reverse-phase HPLC (150×30 mm, 5 micron C-18 column), eluting with a gradient of 70-90% acetonitrile in pH 10 water to provide the title compound as an oil (25.4 mg; 28%).

$^1$H NMR (500 MHz, CDCl$_3$) δ 6.98 (d, J=8.2 Hz, 1H), 6.82 (d, J=2.6 Hz, 1H), 6.66 (dd, J=8.2, 2.6 Hz, 1H), 6.30 (d, J=9.5 Hz, 1H), 6.09 (t, J=55.1 Hz, 1H), 5.85 (dd, J=9.5, 6.0 Hz, 1H), 5.74 (ddt, J=16.8, 10.2, 6.6 Hz, 1H), 5.12-5.02 (m, 2H), 2.94-2.80 (m, 2H), 2.40-2.29 (m, 2H), 2.07 (s, 3H), 2.05-1.90 (m, 2H), 1.64-1.52 (m, 4H), 1.48-1.31 (m, 3H), 1.29-1.17 (m, 1H), 1.01-0.91 (m, 1H). m/z (ES+), [M+H]+: 363.8.

Example 20: Synthesis of CNS222-D2

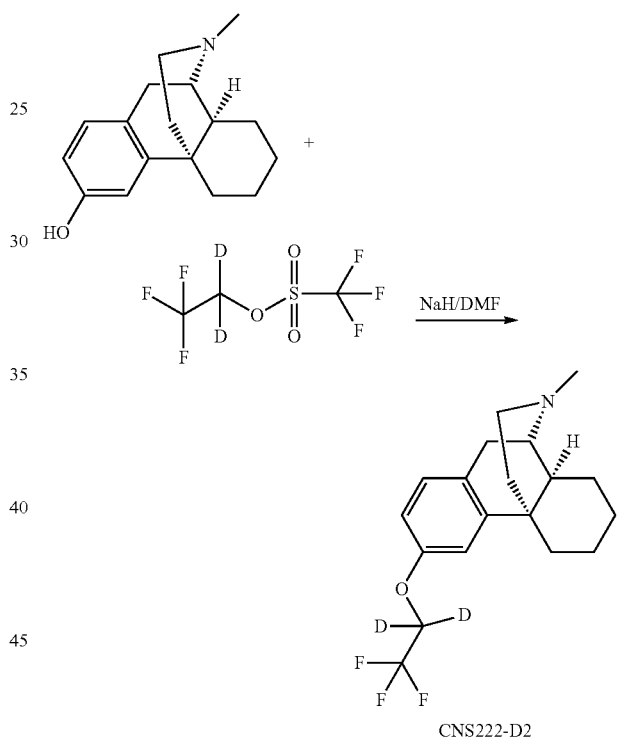

CNS222-D2

The non-deuterated analogue, CNS222, (1S,9S,10S)-4-(2,2,2-trifluoroethoxy)-17-methyl-17-azatetracyclo[7.5.3.0$^{1,}$ $_{10}$.0$^{2,7}$]heptadeca-2(7),3,5-triene, is prepared as described by Melker et al., U.S. Patent application publication No. 2009/0005270.

Dextrorophan free base (64 mg, 0.25 mmol) was dissolved in anhydrous DMF (1 ml) under argon atmosphere. To this solution was added sodium hydride (30 mg, 0.75 mmol) and the resulting mixture was stirred at room temperature under argon for 30 min. The reaction was then cooled to 5° C. and 2,2,2-trifluoroethyl,1,1-d$_2$ trifluoromethanesulfonate (293 mg, 1.25 mmol) was added dropwise. The reaction mixture was allowed to warm to room temperature and stirred under argon over the weekend. The mixture was diluted with ethyl acetate (30 mL) and washed with water (2×8 mL), then brine (8 mL). The organic layer was dried over Na$_2$SO$_4$, filtered and concentrated to give a light yellow oil (50 mg). TLC showed presence of the desired product as major spot. The crude material was purified by column chromatography on silica gel using a gradient of 0.5% NH₄OH/methanol in dichloromethane. Fractions with Rf 0.44 (eluting with 10% NH₄OH/methanol) were collected and concentrated to give 40 mg of product as an oil.

¹H NMR was consistent with the structure of (1S,9S,10S)-4-(1,1-dideuterio-2,2,2-trifluoroethoxy)-17-methyl-17-azatetracyclo[7.5.3.0$^{1,10}$.0$^{2,7}$]heptadeca-2(7),3,5-triene (CNS-222-D2 free base.)

MS calculated for $C_{19}H_{22}D_2F_3NO$ 341.19, found 342.3.

To a solution of CNS-222-D2 free base (40 mg, 0.12 mmol) in ether/EtOAc (0.48 ml/0.3 ml) was slowly added a freshly prepared solution of oxalic acid (26 mg, 0.29 mmol) in diethyl ether (1.86 ml.) No precipitate was formed. The solvent was removed and the residue was re-dissolved in fresh anhydrous ether (1 ml). The mixture was stirred at room temperature for 1.5 hr. The resulting white precipitate was filtered, washed with ether and dried under vacuum to give 15.8 mg of product as white solid.

¹H NMR (499 MHz, DMSO-d6) δ 7.18 (d, J=8.5 Hz, 1H), 7.03-6.87 (m, 2H), 3.61 (s, 1H), 3.16 (t, J=19.3 Hz, 1H), 2.99 (d, J=16.0 Hz, 1H), 2.83 (s, 3H), 1.92 (d, J=12.2 Hz, 1H), 1.75 (t, J=13.8 Hz, 1H), 1.62 (d, J=12.9 Hz, 1H), 1.48 (dd, J=34.8, 13.2 Hz, 2H), 1.31 (dq, J=21.6, 14.3 Hz, 2H), 1.20-1.03 (m, 1H), 0.95 (d, J=13.1 Hz, 1H). ¹³C NMR (126 MHz, DMSO) δ 156.71, 139.51, 129.99, 128.20, 113.60, 112.18, 89.46, 79.45, 62.64, 59.40, 47.50, 42.44, 35.99, 35.12, 25.83, 23.04, 21.92.

MS calculated for $C_{19}H_{22}D_2F_3NO$: m/z=341.19; found m/z=342.2 (M+H)+.

The supernatants from the above process were concentrated under reduced pressure and the residue was treated with diethyl ether. After stirring overnight, a crystalline solid was obtained. Solvent was removed, and the residue (40 mg) was stored under refrigeration.

Example 21: Synthesis of CNS1-D5 oxalate

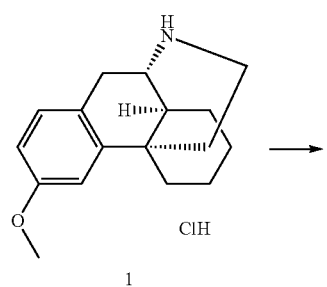

1

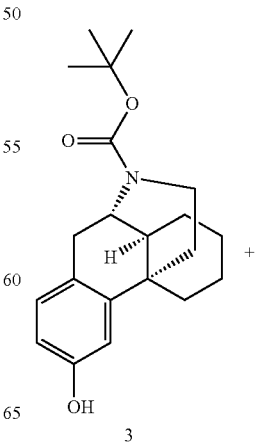

2

NDDX hydrochloride (1), (8.69 g, 29.6 mol) was added to 48% aqueous HBr (297 mmol, 50 mL) and the mixture was stirred for 15 h at reflux. The mixture was cooled to 20° C. and diluted with water (100 mL). The resultant suspension was filtered and the solids washed with water (20 mL) to afford (1S,9S,10S)-17-azatetracyclo[7.5.3.0$^{1,10}$.0$^{2,7}$]heptadeca-2(7),3,5-trien-4-ol hydrobromide (2) as a solid (8.7 g, 91%). ¹H NMR (400 MHz, DMSO-d6) δ 8.74 (s, 2H), 6.99 (d, J=8.2 Hz, 1H), 6.70 (d, J=2.3 Hz, 1H), 6.63 (dd, J=8.3, 2.4 Hz, 1H), 3.66-3.61 (m, 1H), 3.07 (dd, J=18.8, 6.0 Hz, 2H), 2.87 (d, J=18.9 Hz, 1H), 2.48-2.39 (m, 1H), 2.29 (d, J=13.5 Hz, 1H), 1.90-1.81 (m, 1H), 1.70 (td, J=13.6, 4.6 Hz, 1H), 1.60 (d, J=12.7 Hz, 1H), 1.49 (d, J=13.1 Hz, 1H), 1.43 (d, J=11.7 Hz, 2H), 1.38-1.23 (m, 2H), 1.14 (dd, J=26.0, 12.9 Hz, 1H), 0.92 (qd, J=12.8, 3.8 Hz, 1H); m/z (ES+) [M+MeCN+H]+285.6; LCMS (A05); tR=1.59 m.

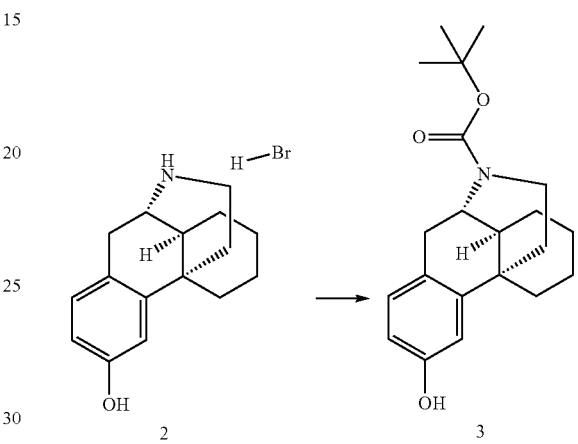

Diisopropylethylamine (14.0 mL, 80.5 mmol) was added to a mixture of 2 (8.70 g, 26.8 mmol) and BOC anhydride (6.16 mL, 26.8 mmol) in DCM (125 mL). The mixture was stirred at 20° C. for 2 h. The mixture was diluted with saturated aqueous NaHCO₃ (150 mL). The organic phase was rinsed with 1 N aqueous HCl (100 mL) and brine (150 mL), dried (Na₂SO₄) and concentrated to afford t-butyl (1S,9S,10S)-4-hydroxy-17-azatetracyclo[7.5.3.0$^{1,10}$.0$^{2,7}$]heptadeca-2,4,6-triene-17-carboxylate (3) as a solid (9.2 g, quant.). ¹H NMR (400 MHz, CDCl₃) δ 6.94 (t, J=9.0 Hz, 1H), 6.76 (d, J=2.7 Hz, 1H), 6.62 (d, J=8.4 Hz, 1H), 4.69 (d, J=33.6 Hz, 1H), 4.26 (d, J=73.0 Hz, 1H), 3.94-3.66 (m, 1H), 3.04 (d, J=7.2 Hz, 1H), 2.70-2.45 (m, 2H), 2.32 (d, J=11.9 Hz, 1H), 1.66 (d, J=10.0 Hz, 2H), 1.60-1.51 (m, 2H), 1.46 (d, J=14.4 Hz, 9H), 1.39-1.22 (m, 4H), 1.17-0.98 (m, 1H); m/z (ES+) [M+H]+=344.6; HPLC (A05) $t_R$=2.69 m.

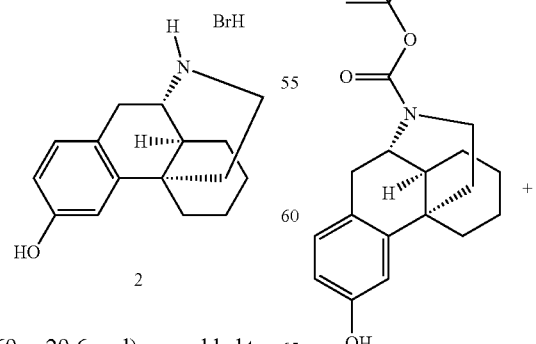

3

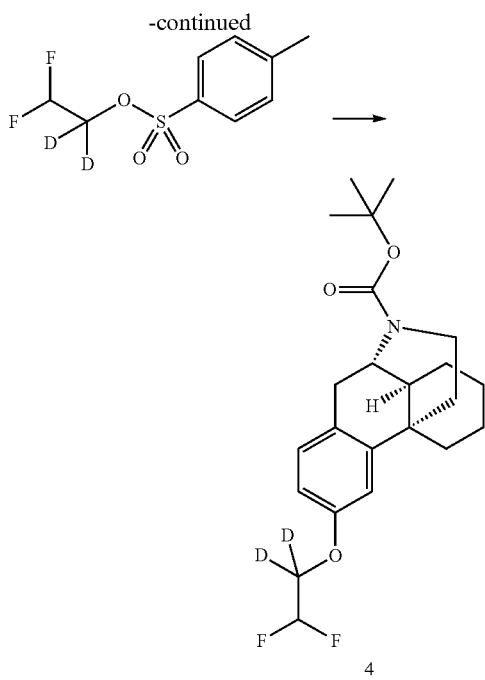

To a solution of (3) (3.00 g, 8.73 mmol) and 1,1-dideuterio-2,2-difluoroethyl 4-methylbenzenesulfonate (2.28 g, 9.57 mmol) in DMF (50 mL) was added $K_2CO_3$ (3.62 g, 26.2 mmol). The mixture was stirred at 80° C. for 16 h, then at 120° C. for 5 h. The mixture was cooled to 20° C., and dry-packed with silica gel. The crude residue was purified by column chromatography on silica gel (80 g cartridge) eluting with mixtures of EtOAc (0-20%) in hexanes to afford t-butyl (1S,9S,10S)-4-(1,1-dideuterio-2,2-difluoroethoxy)-17-aza-tetracyclo-[$7.5.3.0^{1,10}.0^{2,7}$]heptadeca-2,4,6-triene-17-carboxylate (4) as a solid (2.9 g, 81%). $^1$H NMR (400 MHz, $CDCl_3$) δ 7.02 (t, J=8.1 Hz, 1H), 6.85 (d, J=2.5 Hz, 1H), 6.70 (dd, J=8.4, 2.5 Hz, 1H), 6.07 (t, J=55.2 Hz, 1H), 4.27 (d, J=75.0 Hz, 1H), 3.91-3.66 (m, 1H), 3.17-2.98 (m, 1H), 2.72-2.44 (m, 2H), 2.34 (d, J=12.5 Hz, 1H), 1.74-1.42 (m, 4H), 1.50-1.43 (m, J=13.5 Hz, 9H), 1.41-1.18 (m, 5H), 1.12-0.98 (m, 1H). m/z (ES+)[M+H]+=410.7; HPLC (A05) $t_R$=2.96 m.

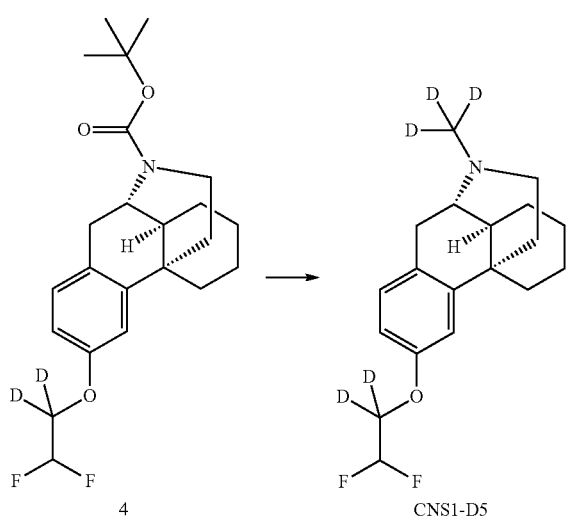

A solution of (4) (600 mg, 1.47 mmol) in THF (10 mL) was added to a suspension of $LiAlD_4$ (198 mg, 4.72 mmol) in THF (5 mL). The mixture was stirred at 20° C. for 18 h. The mixture was then stirred at 60° C. for 5 h. The mixture was cooled to 20° C. and mixed with an aqueous solution of Rochelle's salt (20 mL). The mixture was stirred at 20° C. for 18 h. The mixture was diluted with EtOAc (100 mL) and water (50 mL). The organic phase was rinsed with brine (100 mL), dried ($Na_2SO_4$), filtered, and concentrated to afford crude (1S,9S,10S)-4-(1,1-dideuterio-2,2-difluoroethoxy)-17-(trideuteriomethyl)-17-azatetracyclo[$7.5.3.0^{1,10}.0^{2,7}$]-heptadeca-2,4,6-triene (CNS1-D5) (540 mg, quant.). $^1$H NMR (400 MHz, DMSO-d6) δ 7.05 (d, J=8.2 Hz, 1H), 6.82 (d, J=2.7 Hz, 1H), 6.75 (dd, J=8.4, 2.7 Hz, 1H), 6.34 (t, J=54.6 Hz, 1H), 2.91 (d, J=18.2 Hz, 1H), 2.69 (dd, J=5.2, 3.1 Hz, 1H), 2.50-2.44 (m, 1H), 2.38 (d, J=13.1 Hz, 1H), 2.29 (dd, J=11.7, 2.9 Hz, 1H), 1.90 (td, J=12.2, 3.2 Hz, 1H), 1.70 (dt, J=12.9, 2.9 Hz, 1H), 1.60 (td, J=12.5, 4.8 Hz, 2H), 1.47 (d, J=12.5 Hz, 1H), 1.40-1.10 (m, 5H), 1.04-0.92 (m, 1H); m/z (ES+) [M]+326.5; LCMS (A05); $t_R$=2.00 m.

A solution of oxalic acid (69.0 mg, 0.766 mmol) in IPA (0.5 mL) was added to a solution of CNS1-D5 (199 mg, 0.610 mmol) in IPA (7.5 mL). The mixture was stirred at 20° C. for 30 min, then rested for 1 h. The mixture was filtered and the solids rinsed with IPA (10 mL) and diethyl ether (30 mL) to afford CNS1-D5 oxalate as a solid (153 mg, 60%). $^1$H NMR (300 MHz, MeOD) δ 7.20 (d, J=8.5 Hz, 1H), 6.96 (d, J=2.6 Hz, 1H), 6.89 (dd, J=8.4, 2.5 Hz, 1H), 6.15 (t, J=54.9 Hz, 1H), 3.62 (s, 1H), 3.18 (s, 3H), 2.69 (s, 1H), 2.52 (d, J=13.2 Hz, 1H), 2.14-1.78 (m, 2H), 1.79-1.23 (m, 7H), 1.24-1.04 (m, 1H); m/z (ES+) [M+H]+=327.3; HPLC (QC) $t_R$=2.99 m.

Example 22: Synthesis of N-desmethyl CNS1-D2

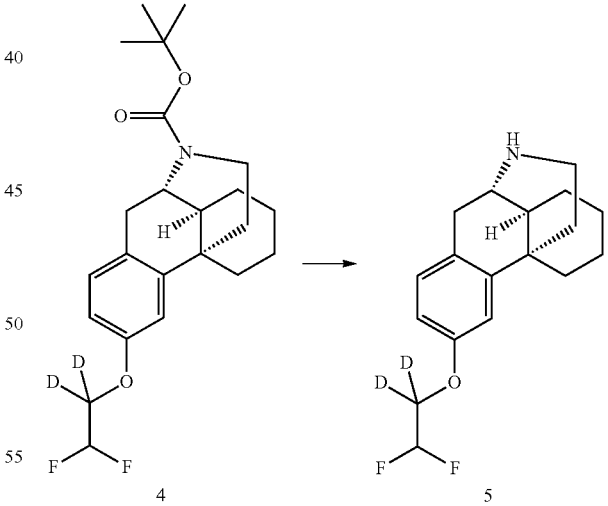

Compound (4), prepared as above (2.20 g, 5.37 mmol) was added to a 4.0 M solution of HCl in dioxane (35.0 mL, 140 mmol), and the mixture was stirred at 20° C. for 2 h. The mixture was diluted with diethyl ether (150 mL) and stored at −20° C. for 16 h. The suspension was filtered, and the solids rinsed with diethyl ether (30 mL), then air dried to afford the hydrochloride of (1S,9S,10S)-4-(1,1-dideuterio-2,2-difluoro-ethoxy)-17-azatetracyclo[$7.5.3.0^{1,10}.0^{2,7}$]heptadeca-2,4,6-triene (5, N-desmethyl CNS1-D2) as a solid (1.48 g, 80%). $^1$H NMR (400 MHz, DMSO-d6) δ 9.13 (s, 2H), 7.15 (d, J=8.4 Hz, 1H), 6.92 (d, J=2.7 Hz, 1H), 6.88 (dd, J=8.4, 2.5 Hz, 1H), 6.36 (t, J=54.5 Hz, 1H), 3.62 (dd, J=5.3, 2.9 Hz, 1H), 3.11 (dd, J=19.2, 6.3 Hz, 1H), 3.00 (dd, J=22.9, 11.1 Hz, 2H), 2.49-2.35 (m, 2H), 1.91 (dt, J=5.4, 2.5 Hz, 1H), 1.73 (td, J=13.6, 4.6 Hz, 1H), 1.60 (d, J=12.9 Hz, 1H), 1.54-1.39 (m, 3H), 1.40-1.22 (m, 2H), 1.21-1.03 (m, 1H), 0.90 (qd, J=12.9, 3.9 Hz, 1H); m/z (ES+) [M+H]+=309.7; HPLC (A05) $t_R$=1.96 m.

The hydrochloride of (5) (600 mg, 1.73 mmol) was stirred vigorously at 20° C. with DCM (20 mL) and saturated aqueous NaHCO$_3$ (20 mL). The phases were separated, the organic phase was collected, dried (Na$_2$SO$_4$) and concentrated to afford the free base (5) (570 mg, 97%). $^1$H NMR (400 MHz, DMSO-d6) δ 7.03 (d, J=8.4 Hz, 1H), 6.81 (d, J=2.5 Hz, 1H), 6.76 (dd, J=8.4, 2.7 Hz, 1H), 6.34 (t, J=54.6 Hz, 1H), 4.09 (brs, 1H), 2.96 (dd, J=17.6, 6.2 Hz, 1H), 2.88 (dd, J=5.7, 3.1 Hz, 1H), 2.64 (d, J=17.6 Hz, 1H), 2.55-2.46 (m, 1H), 2.37 (dd, J=12.6, 3.0 Hz, 1H), 2.35-2.29 (m, 1H), 1.69-1.62 (m, 1H), 1.61-1.53 (m, 1H), 1.51-1.39 (m, 2H), 1.38-1.07 (m, 5H), 0.96-0.81 (m, 1H); m/z (ES+) [M+H]+=310.2; HPLC (QC) $t_R$=1.25 m.

Example 23: Synthesis of CNS27-D2 oxalate

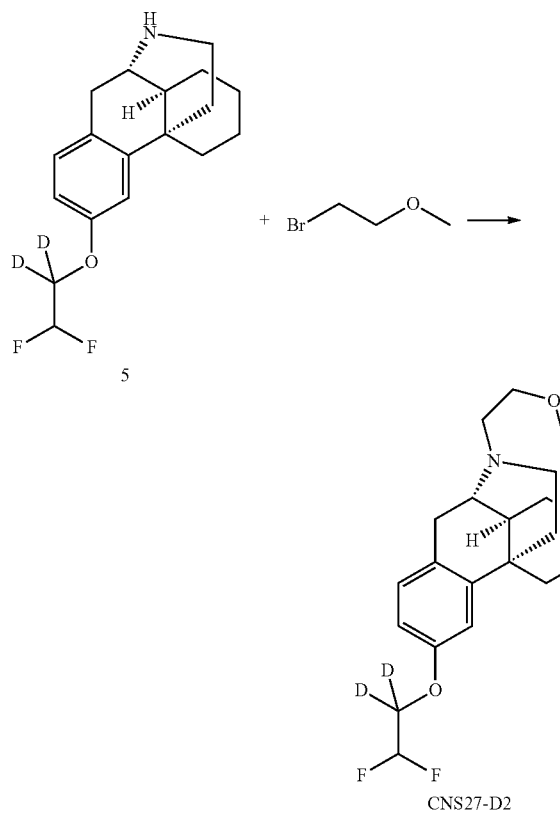

A mixture of compound (5), prepared as above (550 mg, 1.59 mmol), 1-bromo-2-methoxyethane (0.329 mL, 3.50 mmol), and Cs$_2$CO$_3$ (1.04 g, 3.18 mmol) in acetone (16 mL) was stirred at 100° C. for 16 h. The mixture was filtered on a short pad of Celite™ and the pad was rinsed with acetone (20 mL). The filtrate was concentrated in the presence of silica gel. The crude solid was purified by column chromatography on silica gel (40 g cartridge) eluting with mixtures of MeOH containing 5% aqueous (NH$_4$)OH (0-20%) in DCM to afford (1S,9S,10S)-4-(1,1-dideuterio-2,2-difluoroethoxy)-17-(2-methoxyethyl)-17-azatetracyclo[7.5.3.0$^{1,10}$.0$^{2,7}$]-heptadeca-2,4,6-triene (CNS27-D2) as a solid (494 mg, 85%). $^1$H NMR (400 MHz, CDCl$_3$) δ 7.03 (d, J=8.4 Hz, 1H), 6.82 (d, J=2.7 Hz, 1H), 6.67 (dd, J=8.4, 2.7 Hz, 1H), 6.06 (t, J=55.2 Hz, 1H), 3.58-3.44 (m, 2H), 3.35 (s, 3H), 2.97-2.87 (m, 2H), 2.83-2.73 (m, 1H), 2.71-2.52 (m, 3H), 2.31 (d, J=13.7 Hz, 1H), 2.09 (td, J=12.3, 3.1 Hz, 1H), 1.94-1.83 (m, 1H), 1.77 (td, J=12.7, 4.7 Hz, 1H), 1.69-1.57 (m, 1H), 1.56-1.47 (m, 1H), 1.44-1.18 (m, 5H), 1.15-1.00 (m, 1H); m/z (ES+) [M+H]+=368.7; HPLC (A05) $t_R$=2.08 m.

A solution of oxalic acid (121 mg, 1.34 mmol) in IPA (1 mL) was added to a solution of CNS27-D2 (494 mg, 1.34 mmol) in IPA (13 mL). The mixture was chilled to −20° C. for 96 h, and the precipitated solids isolated by filtration. The filtrate was concentrated, and the residue was triturated with a mixture of methyl t-butyl ether (MTBE) (20 mL) and IPA (2 mL), and the precipitated solids isolated by filtration. The collected solids were combined and dried in vacuo to afford CNS27-D2 oxalate as a solid (398 mg, 65%). $^1$H NMR (300 MHz, MeOD) δ 7.19 (d, J=8.5 Hz, 1H), 6.95 (s, 1H), 6.89 (dd, J=8.4, 2.5 Hz, 1H), 6.15 (t, J=54.9 Hz, 1H), 3.79-3.65 (m, 3H), 3.46 (s, 2H), 3.41 (s, 3H), 3.27 (s, 1H), 3.18 (s, 2H), 2.74 (t, J=12.1 Hz, 1H), 2.52 (d, J=13.5 Hz, 1H), 2.10 (d, J=12.3 Hz, 1H), 2.04-1.88 (m, 1H), 1.81-1.50 (m, 4H), 1.42 (dd, J=25.1, 12.2 Hz, 2H), 1.37-1.25 (m, 1H), 1.23-1.04 (m, 1H); m/z (ES+) [M+H]+=368.3; HPLC (QC) $t_R$=3.25 m.

Example 24: Synthesis of CNS28-D5 oxalate

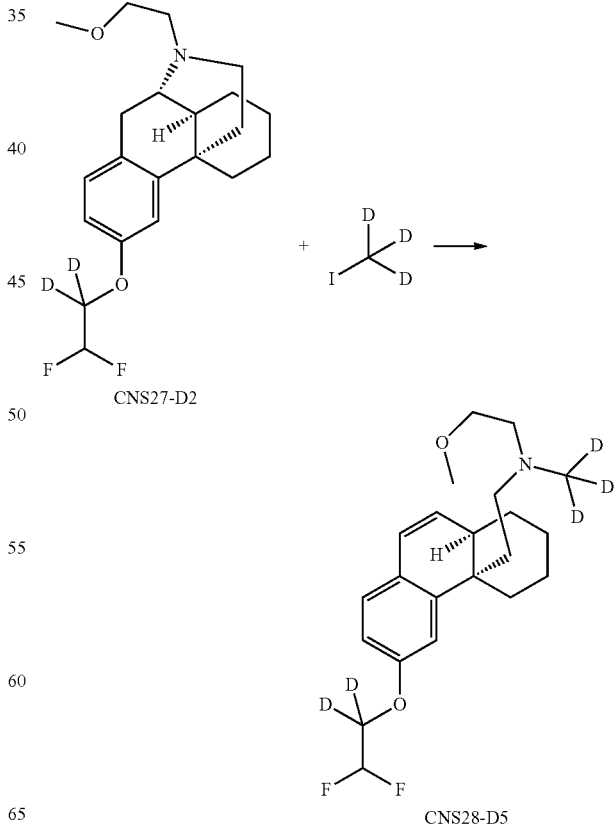

Iodotrideuteriomethane (0.108 mL, 1.74 mmol) was added to a solution of CNS27-D2 (64.0 mg, 0.174 mmol) in DMF (2 mL). The mixture was stirred at 20° C. for 18 h and then at 100° C. for 3 h. The mixture was concentrated without evaporating to dryness. DBU (0.0449 mL, 0.348 mmol) was added, and the mixture was heated to 100° C. for 18 h. The mixture was concentrated to dryness, and the residue was dissolved in MeCN (3 mL). DBU (0.200 mL, 1.55 mmol) was added, and the mixture was heated to 100° C. for 2 h. The mixture was concentrated to ~1.5 mL, and the residue was purified by reverse phase chromatography on C18 silica (30 g cartridge) eluting with a step gradient of MeCN (5-100%) in aqueous ammonium formate buffer to afford 2-[(4aS,10aR)-6-(1,1-dideuterio-2,2-difluoro-ethoxy)-2,3,4,10a-tetrahydro-1H-phenanthren-4a-yl]-N-(2-methoxyethyl)-N-(trideuteriomethyl)ethanamine (CNS28-D5) (48 mg, 72%). m/z (ES+) [M+H]+=384.9; HPLC (A05) $t_R$=2.18 m.

A solution of oxalic acid (5.00 mg, 0.0555 mmol) in IPA (0.05 mL) was added to a solution of CNS28-D5 (20.0 mg, 0.0520 mmol) in IPA (0.5 mL). The mixture was chilled to −20° C. for 18 h, and the solids collected by filtration and rinsed with ether (5 mL). The filtrate was concentrated and triturated with ether (5 mL) to afford additional solids. The solids were combined and dried under high vacuum to afford CNS28-D5 oxalate as a solid (19.2 mg, 78%). $^1$H NMR (400 MHz, MeOD) δ 7.09 (d, J=8.4 Hz, 1H), 6.93 (d, J=2.1 Hz, 1H), 6.85 (dd, J=8.2, 2.3 Hz, 1H), 6.39 (d, J=9.4 Hz, 1H), 6.17 (t, J=55.0 Hz, 1H), 5.92 (dd, J=9.5, 6.1 Hz, 1H), 3.58-3.37 (m, 2H), 3.27 (s, 3H), 3.16 (m, 3H), 3.23-3.10 (m, 3H), 2.74 (s, 1H), 2.46 (d, J=7.0 Hz, 1H), 2.24 (t, J=10.8 Hz, 1H), 2.18-2.06 (m, 1H), 1.63 (d, J=11.5 Hz, 4H), 1.48-1.23 (m, 3H), 0.94 (dd, J=22.3, 11.9 Hz, 1H); m/z (ES+) [M+H]+=385.3; HPLC (QC) $t_R$=3.95 m.

Example 25: Synthesis of CNS29-D5 oxalate

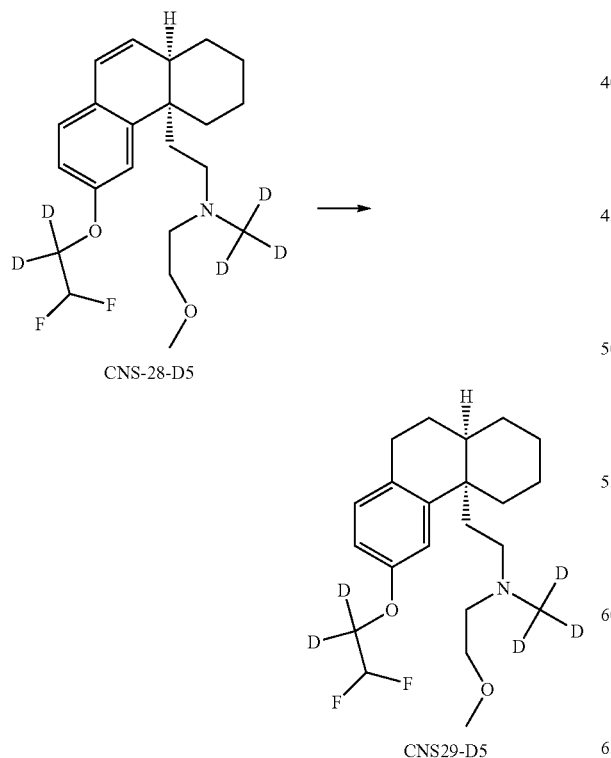

A mixture of CNS28-D5 (48.6 mg, 0.126 mmol) and PtO$_2$ (9.00 mg, 0.0396 mmol) in EtOH (3 mL) was stirred under a hydrogen atmosphere at 20° C. for 24 h. The mixture was filtered on a short pad of Celite™, and the filtrate concentrated to afford 2-[(4a5,10aR)-6-(1,1-dideuterio-2,2-difluoro-ethoxy)-2,3,4,9,10,10a-hexahydro-1H-phenanthren-4a-yl]-N-(2-methoxyethyl)-N-(trideuteriomethyl)ethanamine (CNS29-D5) (45.2 mg, 93%). m/z (ES+) [M+H]+=387.4; HPLC (A05) $t_R$=2.40 m.

Oxalic acid (11.2 mg, 0.125 mmol) was added to a solution of CNS29-D5 (45.2 mg, 0.117 mmol) in IPA (1.2 mL). The mixture was stirred at 20° C. for 30 min. The mixture was filtered, and the solids rinsed with ether (5 mL) then collected and dried under high vacuum to afford CNS29-D5 oxalate as a solid (35 mg, 63%). $^1$H NMR (500 MHz, MeOD) δ 7.04 (d, J=8.5 Hz, 1H), 6.88 (d, J=2.7 Hz, 1H), 6.77 (dd, J=8.4, 2.7 Hz, 1H), 6.14 (t, J=55.0 Hz, 1H), 3.65-3.53 (m, 2H), 3.31 (s, 3H), 3.27 (t, J=4.7 Hz, 2H), 3.12-2.93 (m, 2H), 2.87-2.69 (m, 2H), 2.26 (s, 1H), 2.14-2.06 (m, 1H), 2.04-1.92 (m, 2H), 1.84-1.65 (m, 3H), 1.65-1.49 (m, 3H), 1.49-1.29 (m, 3H); m/z (ES+) [M+H]+=387.3; HPLC (QC) $t_R$=4.09 m.

Example 26: Synthesis of CNS34-D2 oxalate

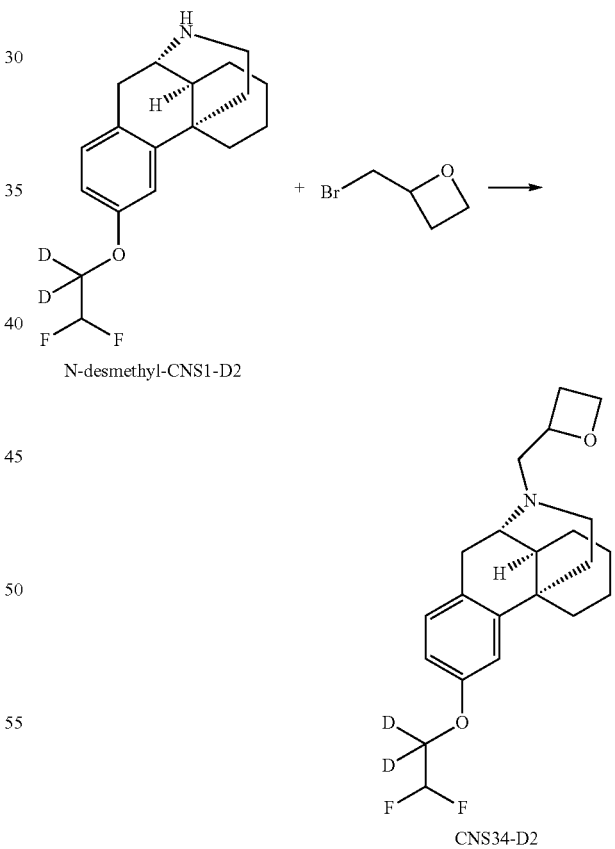

2-(Bromomethyl)oxetane (0.0190 mL, 0.197 mmol) was added to a mixture of N-desmethyl-CNS1-D2 hydrochloride (50.0 mg, 0.145 mmol) and Cs$_2$CO$_3$ (0.0942 g, 0.289 mmol) in acetone (1.5 mL). The mixture was stirred at 20° C. for 6 h. The mixture was then heated to 80° C. for 18 h. 2-(bromomethyl)oxetane (0.0200 mL, 0.208 mmol) was added and the mixture was heated to 80° C. for 18 h. The mixture was filtered on a microporous filter and the filter was rinsed with acetone (5 mL). The filtrate was concentrated in the presence of silica gel. The crude solid was purified by column chromatography on silica gel (40 g cartridge) eluting with mixtures of MeOH containing 5% aqueous $(NH_4)OH$ (0-20%) in DCM. The residue containing the title compound was purified by reverse phase chromatography on C18 (30 g cartridge) eluting with mixtures of MeCN (10-100%) in ammonium carbonate buffer. The residue containing the title compound was purified by reverse phase chromatography on C18 (4 g cartridge) eluting with mixtures of MeCN (10-100%) in ammonium formate buffer. The fractions containing the title compound were basified with aqueous $(NH_4)OH$ and concentrated. The residue was mixed with DCM (10 mL) and 1 M NaOH (10 mL). The organic phase was collected, dried $(Na_2SO_4)$ and concentrated to afford (1S, 9S,10S)-4-(1,1-dideuterio-2,2-difluoro-ethoxy)-17-(oxetan-2-ylmethyl)-17-azatetracyclo[7.5.3.0$^{1,10}$.0$^{2,7}$]heptadeca-2,4,6-triene (CNS34-D2) as a mixture of diastereomers (7.7 mg, 7%). $^1$H NMR (500 MHz, MeOD) δ 7.19 (d, J=8.5 Hz, 1H), 6.94 (t, J=2.4 Hz, 1H), 6.91-6.85 (m, 1H), 6.14 (t, J=54.9 Hz, 1H), 5.25 (dd, J=16.2, 7.4 Hz, 1H), 4.73-4.65 (m, 1H), 4.65-4.56 (m, 1H), 3.80 (ddd, J=41.5, 13.7, 9.3 Hz, 1H), 3.64-3.56 (m, 1H), 3.39-2.94 (m, 4H), 2.91-2.78 (m, 1H), 2.76-2.61 (m, 1H), 2.56-2.43 (m, 2H), 2.16-2.08 (m, 1H), 2.02-1.92 (m, 1H), 1.70 (d, J=11.7 Hz, 1H), 1.64-1.48 (m, 4H), 1.47-1.36 (m, 2H), 1.34-1.21 (m, 1H), 1.18-1.05 (m, 1H); m/z (ES+) [M+H]+=380.2; HPLC (A05) $t_R$=2.09 m.

Testing of Drug Stability in Human Liver Microsomes

This assay involves exposing a test compound to vesicles which contain the contents of digestive organelles (endoplasmic reticula) derived from human liver cells. The tests were done by Microconstants Inc., San Diego, Calif., using methods substantially as described in J. R. Hill, "In vitro drug metabolism using liver microsomes," Curr. Protocols Pharmacol., Chapter 7, Unit 7.8 (2004), John Wiley & Sons, Inc.

The results, in Table 1 below, indicate the percentage decomposition of the test compound after 1 hour. The compounds identified as CNS1 and CNS2 and their deuterated analogues are metabolized and degraded less rapidly than DM, and are of interest when judged by this particular result. Although degraded as rapidly, or even more rapidly than DM, other compounds remain of interest due to their receptor binding activities, as detailed further below.

TABLE 1

Human Microsomal Decomposition

| COMPOUND | $t_{1/2}$ (min) | % decomposition at 1 hour |
| --- | --- | --- |
| Dextromethorphan (DM) | 35 | 69 |
| Dimemorphan (DIM) | 22 | |
| CNS1 | | 6.1 |
| CNS1-D2 | 123 | |
| CNS1-D5 | >240 | 9.7 |
| CNS2 | | 15.4 |
| CNS4 | | 100 |
| CNS6 | | 56 |
| CNS6-A1-D2 | 60 | |
| CNS10 | | 98.4 |
| CNS22 | 36 | |
| CNS23-D2 | 32 | |
| CNS25 | 35 | |

TABLE 1-continued

Human Microsomal Decomposition

| COMPOUND | $t_{1/2}$ (min) | % decomposition at 1 hour |
| --- | --- | --- |
| CNS26 | 14 | |
| CNS27 | >960 | 2.8 |
| N-desmethyl CNS1-D2 | >240 | 10.1 |

Receptor Binding Assays

In vitro binding assays for the phencyclidine site of NMDA-type glutamate receptors, and for sigma-1 receptors, both of which are known to be bound by DM, were conducted by Sekisui Medical Co., Ltd. of Ibaraki, Japan. In these assays, DM acts as an antagonist at NMDA receptors, which are excitatory in their effects, thereby allowing DM to reduce, calm, and modulate unwanted neuronal activity in neuronal networks that are activated by glutamate agonist activity at NMDA receptors. DM acts as an agonist at sigma-1 receptors, which are inhibitory receptors, thereby allowing DM to reduce unwanted neuronal activity by a second mechanism. Assays for sigma-1 and NMDA (phencyclidine site) receptor affinities, based on inhibition of radioligand binding, provided the results shown in Table 2 below.

TABLE 2

Inhibition of Radioligand Binding at σ1 and NMDA Receptors

| COMPOUND | Sigma-1 IC$_{50}$ (nM) | Sigma-1 Ki (nM) | NMDA IC$_{50}$ (μM) | NMDA Ki (μM) |
| --- | --- | --- | --- | --- |
| Dextromethorphan (DM) | 137 | 96.3 | 6.82 | 4.52 |
| Dextorphan (DX) | 259 | 182 | 1.53 | 1.11 |
| Dimemorfan (DIM) | 527 | 371 | >30 | — |
| CNS6 | 172 | 121 | >30 | — |
| CNS6-A1-D2 | 21.8 | 15.3 | >30 | — |
| CNS6-A2 | 247 | — | 7.08 | — |
| CNS7-M | >10000 | — | — | — |
| CNS22 | 29.1 | 20.5 | 5.25 | 3.81 |
| CNS23-D2 | 11.1 | 7.8 | >30 | — |
| CNS25 | 28.4 | 20 | 14.6 | 10.6 |
| CNS26 | 79.1 | 55.6 | 8.85 | — |
| CNS1-D2 | 57.8 | 40.6 | >30 | — |
| CNS1-D5 | | 22 | | 9.9 |
| CNS-222 | 50.0 | — | — | — |
| CNS27-D2 | | 1.6 | | >23 |
| N-desmethyl CNS1-D2 | | 70 | | 3.08 |

Results obtained in the above assays are industry-accepted proxies for likely in vivo DM-like activity. "Sigma, PCP, and NMDA receptors", E. B. De Souza et al., eds, NIDA Research Monograph 133, (1993) National Institute on Drug Abuse, Rockville Md. In vivo assays in laboratory animals can be used to establish pharmacokinetic parameters, including the ability of an analog to cross the blood-brain barrier; and human clinical trials of the most promising candidate(s) can establish safety and dosing requirements, and ultimately, serve to demonstrate clinically-proven benefits.

Permeability Assay

The human colon carcinoma cell Caco-2 provides a well-established and effective model for predicting intestinal absorption of chemicals, and in determining the mechanism of transport. When grown in culture, these cells form a well-differentiated, polarized monolayer that possess barrier properties comparable to human intestine in vivo, which is well suited to measurement of transport rates of compounds across the monolayer. The method is used to assess the bidirectional permeability of a test compound, from the apical to the basolateral side (A-B) of a Caco-2 cell monolayer membrane, and vice versa (B-A). R. B. van Breemen, Y. Li, "Caco-2 cell permeability assays to measure drug absorption," *Expert Opin. Drug Metab. Toxicol.*, 1:175-185 (2005). The transport rate of a compound across the monolayer is highly predictive of the in vivo absorption of the compound across the gut wall, and the Caco-2 permeability assay is an FDA-recommended method for evaluating the absorption of orally-administered drugs. Results of this assay for selected reference drugs and compounds of the invention are set out in Table 3.

TABLE 3

| COMPOUND | Caco-2 Permeability | | | |
|---|---|---|---|---|
| | Papp (A-B) $10^{-6}$ cm/s | | Papp (B-A) $10^{-6}$ cm/s | |
| | 0.1 μM | 1 μM | 0.1 μM | 1 μM |
| DM | 15.9 | 19 | 10.8 | 14.2 |
| CNS1-D5 | 14.4 | 18.4 | 12.5 | 15.4 |
| CNS27-D2 | 10.2 | 11.6 | 9.76 | 13.1 |
| N-desmethyl CNS1-D2 | 9.71 | 10.8 | 6.33 | 10.1 |
| | 1 μM | 10 μM | 1 μM | 10 μM |
| Propranolol | 17.5 | 21.2 | 16.3 | 39 |

Cardiac Potassium Channel (hERG) Assays

The human ether-a-go-go related gene (hERG) encodes the inward-rectifying voltage-gated potassium channel (IKr) in the heart, which is involved in cardiac repolarization. Inhibition of the hERG current causes QT interval prolongation, potentially resulting in ventricular tachyarrhythmia, and the detection of this potential liability is desirable at an early stage of drug discovery. $IC_{50}$ and Ki values were determined by Sekisui Medical Co., Ltd., Ibaraki, Japan, using a radioligand ($^3$H-astemizole) binding assay with human recombinant hERG.

Opiate Assays

Activation of the κ opioid receptor produces analgesia, but also causes dysphoria and psychosis. The κ receptor is also largely responsible for the constipation-inducing effect of opiates. Binding affinity for the κ opioid receptor was determined by Sekisui Medical Co., Ltd., Ibaraki, Japan, using a radioligand ($^3$H-diprenorphine) binding assay with membrane preparations from a recombinant cell line expressing the receptor (Eurofins DiscoverX Corp., Fremont Calif., product No. HTS095.)

The μ opioid receptor is the principal target of endogenous opioid peptides and opioid analgesic agents, for which [D-Ala$^2$, N-Me-Phe$^4$, Gly$^5$-ol]-enkephalin (DAMGO) is a standard ligand. Binding affinity for the μ opioid receptor was determined by Sekisui Medical Co., Ltd., Ibaraki, Japan, using a radioligand ($^3$H-diprenorphine) binding assay with membrane preparations from a CHO-K1 recombinant cell line expressing the receptor (Perkin-Elmer Inc., Waltham, Mass., product No. ES-542-M.)

Serotonin Transporter (SERT) Assay

The serotonin transporter (SERT) is a monoamine transporter protein that transports serotonin from the synaptic cleft back to the presynaptic neuron (serotonin reuptake.) Serotonin modulates emotional states in humans, and inhibition of SERT activity is the basis for the SSRI class of antidepressants. Binding affinity for the SERT receptor was determined by Sekisui Medical Co., Ltd., Ibaraki, Japan, using a radioligand ($^3$H-imipramine) binding assay with cell membranes prepared from HEK-293 cells stably transfected with human serotonin transporter receptor (Perkin-Elmer Inc., Waltham, Mass., product No. RBHS™.)

Results of the above assays, carried out with selected compounds and standards, are presented in Table 4.

TABLE 4

Receptor binding of selected compounds

| COMPOUND | hERG K channel | | Opiate κ | | Opiate μ | | SERT | |
|---|---|---|---|---|---|---|---|---|
| | $IC_{50}$ (nm) | Ki (nM) | $IC_{50}$ (nm) | Ki (nM) | $IC_{50}$ (nm) | Ki (nM) | $IC_{50}$ (nm) | Ki (nM) |
| Quinidine | 20,900 | 4,500 | | | | | | |
| DM | 49,100 | 10,600 | 39,900 | 16,000 | 51,700 | 9,580 | 5.5 | 3.3 |
| Astemizole | 5.59 | 1.2 | | | | | | |
| U-69593 | | | 3.04 | 1.22 | | | | |
| DAMGO | | | | | 32.7 | 6.06 | | |
| Imipramine | | | | | | | 3.11 | 1.85 |
| CNS1-D5 | 34,500 | 7,480 | 29,800 | 12,000 | 54,700 | 10,100 | 44.1 | 26.2 |
| CNS27-D2 | 22,300 | 4,800 | 28,800 | 11,600 | 124,000 | 23,000 | 2,680 | 1,590 |
| N-desmethyl CNS1-D2 | 26,600 | 5,730 | 37,700 | 15,200 | 142,000 | 26,300 | 470 | 279 |

The preceding description has disclosed a set of analogs of dextromethorphan which have combinations of traits that render them useful as alternatives to dextromethorphan, and/or have independent pharmacological properties of their own. Although this invention has been exemplified for purposes of illustration and description by reference to certain specific embodiments, it will be apparent to those skilled in the art that various modifications, alterations, and equivalents of the illustrated examples are possible. Any such changes which derive in an obvious way from the teachings herein, and which do not depart from the spirit and scope of the invention, are deemed to be within the scope of the invention and the appended claims.

We claim:

1. A compound of formula I

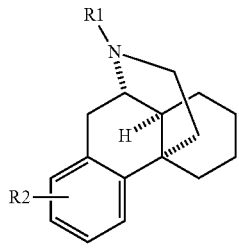

wherein R1 is selected from the group consisting of H, CD$_3$, C$_3$-C$_4$ alkenyl, C$_1$-C$_4$ alkyl, C$_3$-C$_5$ cycloalkyl, (C$_3$-C$_5$ cycloalkyl)methyl, and oxetanylmethyl; and R2 is one or more substituents selected from the group consisting of halogen, pyridylmethyl, C$_1$-C$_4$ alkyl, and C$_1$-C$_4$ alkoxy; with the proviso that at least one of the one or more R2 substituents is C$_2$-C$_4$ alkoxy substituted with one or more fluorine atoms and one or more deuterium atoms.

2. The compound according to claim 1, wherein R2 is 2,2-dideuterio-1,1,1-trifluoroethoxy.

3. The compound according to claim 1, wherein R1 is CD$_3$.

4. The compound according to claim 2, wherein R1 is CD$_3$.

5. A pharmaceutical composition comprising one or more pharmaceutically acceptable excipients, and further comprising a compound of formula I

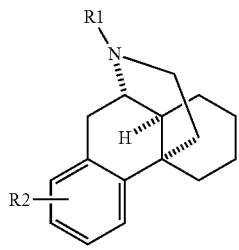

or a pharmaceutically acceptable salt thereof, wherein R1 is selected from the group consisting of H, CD$_3$, C$_3$-C$_4$ alkenyl, C$_1$-C$_4$ alkyl, C$_3$-C$_5$ cycloalkyl, (C$_3$-C$_5$ cycloalkyl)methyl, and oxetanylmethyl; and R2 is one or more selected from the group consisting of halogen, pyridylmethyl, C$_1$-C$_4$ alkyl, and C$_1$-C$_4$ alkoxy, with the proviso that at least one of the one or more R2 is C$_2$-C$_4$ alkoxy substituted with one or more fluorine atoms and one or more deuterium atoms.

6. The composition according to claim 5, wherein R2 is 2,2-dideuterio-1,1,1-trifluoroethoxy.

7. The composition according to claim 5, wherein R1 is CD$_3$.

8. The composition according to claim 6, wherein R1 is CD$_3$.

9. A method of alleviating pseudobulbar affect, in a subject in need of such alleviation, which comprises administering to the subject an effective amount of a compound according to claim 1.

10. A method of alleviating pseudobulbar affect, in a subject in need of such alleviation, which comprises administering to the subject an effective amount of a compound according to claim 2.

11. A method of alleviating pseudobulbar affect, in a subject in need of such alleviation, which comprises administering to the subject an effective amount of a compound according to claim 3.

12. A method of alleviating pseudobulbar affect, in a subject in need of such alleviation, which comprises administering to the subject an effective amount of a compound according to claim 4.

13. A method of alleviating pain, in a subject in need of such alleviation, which comprises administering to the subject an effective amount of a compound according to claim 1.

14. A method of alleviating pain, in a subject in need of such alleviation, which comprises administering to the subject an effective amount of a compound according to claim 2.

15. A method of alleviating pain, in a subject in need of such alleviation, which comprises administering to the subject an effective amount of a compound according to claim 3.

16. A method of alleviating pain, in a subject in need of such alleviation, which comprises administering to the subject an effective amount of a compound according to claim 4.

* * * * *